United States Patent
Cho et al.

(10) Patent No.: US 9,248,202 B2
(45) Date of Patent: Feb. 2, 2016

(54) TWO-PHOTON PROBE FOR DETECTING COPPER(II) ION AND QUANTITATIVE ESTIMATION OF COPPER(II) ION IN HUMAN TISSUE USING THE SAME

(71) Applicants: Korea University Research and Business Foundation, Seoul (KR); SFC CO., LTD., Chungcheongbuk-do (KR)

(72) Inventors: Bong-Rae Cho, Seoul (KR); Dong Eun Kang, Seoul (KR); Chang Su Lim, Seoul (KR); Ji Yeon Kim, Seoul (KR); Eun Sun Kim, Seoul (KR); Hoon Jai Chun, Seoul (KR)

(73) Assignees: Korea University Research and Business Foundation, Seoul (KR); SFC Co. Ltd., Chungcheongbuk-do (KR)

( * ) Notice: Subject to any disclaimer, the term of this patent is extended or adjusted under 35 U.S.C. 154(b) by 0 days.

(21) Appl. No.: 14/463,116

(22) Filed: Aug. 19, 2014

(65) Prior Publication Data

US 2015/0306252 A1    Oct. 29, 2015

(30) Foreign Application Priority Data

Apr. 23, 2014  (KR) .................. 10-2014-0048761

(51) Int. Cl.
| | |
|---|---|
| *C07D 405/14* | (2006.01) |
| *C12Q 1/02* | (2006.01) |
| *A61K 49/00* | (2006.01) |
| *C07D 401/14* | (2006.01) |

(52) U.S. Cl.
CPC .......... *A61K 49/0052* (2013.01); *C07D 401/14* (2013.01); *C07D 405/14* (2013.01); *C12Q 1/02* (2013.01)

(58) Field of Classification Search
None
See application file for complete search history.

(56) References Cited

FOREIGN PATENT DOCUMENTS

KR    1020130039680    4/2013

OTHER PUBLICATIONS

Zhu et al. Scientific Reports 3:2933, pp. 1-7 (2013) available online at www.nature.com/scientificreports.*
Kang et al. Analytical Chemistry vol. 86(11), pp. 5353-5359 (Apr. 21, 2014).*
Gaggelli, Elena, et al., "Copper Homeostasis and Neurodegenerative Disorders (Alzheimer's, Prion, and Parkinson's Diseases and Amyotrophic Lateral Sclerosis)," Chem. Rev., 2006, vol. 106, pp. 1995-2044.
Macreadie, Ian G., "Copper transport and Alzheimer's disease," Eur. Biophys. J., 2008, vol. 37, p. 295-300.
Georgopoulos, P.D., et al., "Environmental Copper: Its Dynamics and Human Exposure Issues," J. of Toxicology & Environmental Health, Part B, 2001, vol. 4, pp. 341-394.
Helmchen, F., et al., "Deep tissue two-photon microscopy," Nature Methods, 2005, vol, 2, No. 12, pp. 932-940.
Zipfel, Warre R., et al., "Nonlinear magic: multiphoton microscopy in the biosciences," Nature Biotechnology, 2003, vol. 21, No. 11, pp. 1369-1377.
Kim, H.M., et al., "Two-Photon Probes for Intracellular Free Metal Ions, Acidic Vesicle, and Lipid Rafts in Live Tissues," Accounts of Chemical Research, vo. 2009, vol. 42, No. 7, pp. 863-872.
Kucharzewski, M., et al., "Selenium, Copper, and Zinc Concentrations in Intestinal Cancer Tissue and in Colon and Rectum Polyps," Biological Trace Element Resarch, 2003, vol. 92.

\* cited by examiner

*Primary Examiner* — Emily Bernhardt
(74) *Attorney, Agent, or Firm* — Duane Morris LLP; J. Rodman Steele, Jr.; Gregory M. Lefkowitz

(57) ABSTRACT

The present disclosure relates to a two-photon probe for in-vivo imaging, having high selectivity for copper(II) ion, and a method for quantitatively estimating copper(II) on ($Cu^{2+}$) in vivo using the same. The two-photon probe according to the present disclosure can detect intracellular free copper(II) on for a long period of time with a penetration depth greater than 90 μm in living cells and tissues without the problems of mistargeting and photobleaching and can quantitatively estimate copper(II) on concentration in vivo using the ratio of blue emission intensity at 400-450 nm and red emission intensity at 550-650 nm.

13 Claims, 10 Drawing Sheets

TWO-PHOTON PROBE FOR DETECTING COPPER(II) ION AND QUANTITATIVE ESTIMATION OF COPPER(II) ION IN HUMAN TISSUE USING THE SAME

CROSS-REFERENCE TO RELATED APPLICATIONS

This application claims priority under 35 U.S.C. §119 to Korean Patent Application No. 10-2014-0048761 filed on Apr. 23, 2014 in the Korean Intellectual Property Office, the disclosure of which is incorporated herein by reference in its entirety.

TECHNICAL FIELD

The present disclosure relates to a novel compound that can be used as a two-photon probe for detecting copper(II) ion ($Cu^{2+}$) in vivo and a method for quantitatively estimating copper(II) ion ($Cu^{2+}$) in vivo using the same.

BACKGROUND

Copper on is an essential metal ion found in various organs and plays crucial roles in living systems as cofactors of cytoplasmic enzymes, mitochondrial enzymes and membrane-bound oxidases in production of cellular energy, reduction of oxygen molecules, signal transduction, or the like. Copper(I) ion ($Cu^+$) in reduced state is internalized in cells but copper (II) ion ($Cu^{2+}$) in oxidized state is often found in cells under oxidative environment. Abnormality in the regulation of copper ion level may cause severe diseases such as Menkes disease, Wilson's disease, Alzheimer's disease and prion disease and increased copper ion level in the body may cause gastrointestinal disorders, damage to the liver and kidneys, and so forth (Gaggelli, E.; Kozlowski, H.; Valensin, D.; Valensin, G. *Chem. Rev.* 2006, 106, 1995; Macreadie, I. G. *Eur. Biophys. J. Biophy.* 2008, 37, 295; Georgopoulos, P. G.; Roy, A.; Yonone-Lioy, M. J.; Opiekun, R. E.; Loy, P. J. *J. Toxicol. Env. Heal. B* 2001, 4, 341).

Total-reflection X-ray fluorescence (TRXRF) and atomic absorption spectroscopy are available as methods for quantitatively measuring copper on in normal and abnormal tissues. However, these methods are incapable of differentiating the oxidation state of copper and are not suitable for quantitative measurement of copper on level in vivo due to low detection sensitivity (Kucharzewski, M.; Braziewicz, J.; Majewska, U.; Gozdz, S. *Biol. Trace Elem. Res.* 2003, 92, 1).

Two-photon microscopy can solve the above problems and allows quantitative measurement of metal ions in vivo. The two-photon microscopy is a technique that uses two near-infrared photons with energy lower than that of confocal microscopy for excitation and allows imaging up to a very high depth inside cells (Helmchen, F.; Denk, W. *Nat. Methods* 2005, 2, 932; Zipfel, W. R.; Williams, R. M.; Webb, W. W. *Nat. Biotechnol.* 2003, 2, 1369; Kim, H. M.; Cho, B. R. Acc. *Chem. Res.* 2009, 42, 863; Kim, H. M.; Cho, B. R. *Chem. Asian J.* 2011, 6, 58).

Korean Patent Publication No. 2013-0039680 discloses a two-photon fluorescent dye selective for copper(I) ion and a manufacturing method thereof. Korean Patent Registration No. 886,722 discloses a two-photon dye capable of monitoring magnesium in the cytoplasm in real time and a monitoring method using the same. And, Korean Patent Registration No. 976,623 discloses a two-photon dye capable of monitoring calcium in cells in real time. Although various two-photon probes for detecting metal ions in vivo have been developed, development of a two-photon probe having selectivity for copper(II) on has not been reported. Accordingly, development of a two-photon probe capable of selectively detecting and quantitating the biologically important copper(II) on is needed.

SUMMARY

The present disclosure is directed to providing a compound having high selectivity and sensitivity for copper(II) ion, having a penetration depth higher than 90 μm in living cells and tissues and being capable of detecting intracellular free copper(II) ion in tissues and cells for a long period of time without the problems of mistargeting and photobleaching, thus being applicable as a two-photon probe for in-vivo imaging, and a method for preparing the same.

The present disclosure is also directed to providing a method for quantitatively estimating copper(II) ion concentration in vivo using the compound.

In an aspect, the present disclosure provides a compound represented by [Chemical Formula 1]:

[Chemical Formula 1]

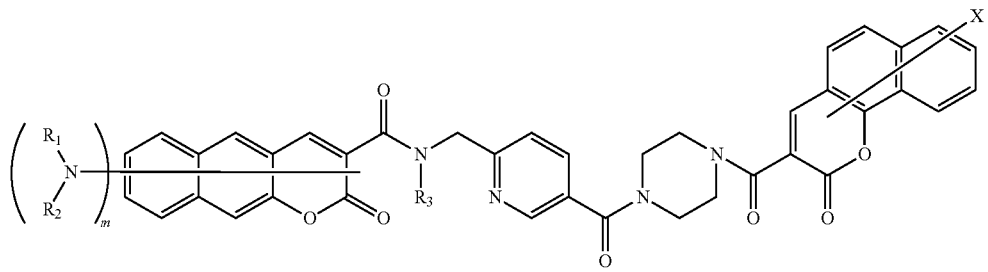

wherein
each of $R_1$, $R_2$ and $R_3$, which are identical or different, is independently hydrogen or $C_1$-$C_{10}$ substituted or unsubstituted alkyl,
X is —$OCH_2(CH_2OCH_2)_nCH_2OCH_3$,
the substituted alkyl is substituted with a substituent selected from a group consisting of halogen, trifluoromethyl, amino, $C_1$-$C_5$ alkyl, $C_1$-$C_5$ alkoxy, hydroxyl, $C_1$-$C_5$ carboxyl, cyano, phenyl and benzyl,
m is an integer from 1 to 3 and
n is an integer from 1 to 6.

In an exemplary embodiment of the present disclosure, the $C_1$-$C_{10}$ substituted or unsubstituted alkyl may be selected from a group consisting of methyl, ethyl, propyl, isopropyl, butyl, sec-butyl, tert-butyl, pentyl, hexyl, heptyl, octyl, nonyl and decyl.

In an exemplary embodiment of the present disclosure, the compound represented by [Chemical Formula 1] may be a compound represented by [Chemical Formula 2]:

[Chemical Formula 2]

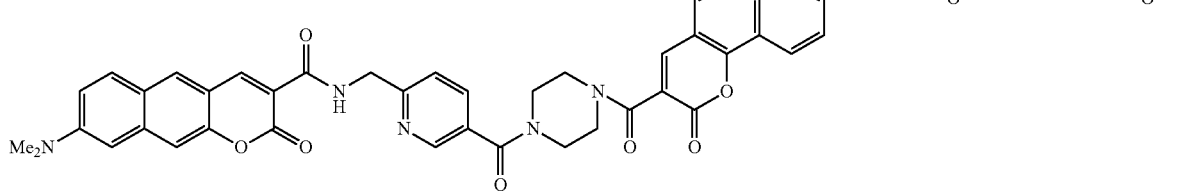

wherein Me stands for methyl.

In an exemplary embodiment of the present disclosure, the compound represented by [Chemical Formula 1] may have selectivity for copper(II) ion.

In another exemplary embodiment of the present disclosure, the compound represented by [Chemical Formula 1] may exhibit two-photon absorption and emission.

In another exemplary embodiment of the present disclosure, the compound represented by [Chemical Formula 1] may allow in-vivo imaging through two-photon absorption and emission.

In another exemplary embodiment of the present disclosure, the compound represented by [Chemical Formula 1] may have a penetration depth higher than 90 μm in living cells and tissues, In another aspect, the present disclosure provides a two-photon probe compound for detecting copper(II) ion having a structure in which a compound exhibiting red emission, as a fluorophore and copper(II) ion chelator, and a compound exhibiting blue emission, as an internal reference, are bound to both ends of a piperazine group.

In an exemplary embodiment of the present disclosure, the compound exhibiting red emission as a fluorophore and copper(II) on chelator may be a compound represented by [Chemical Formula 3]:

[Chemical Formula 3]

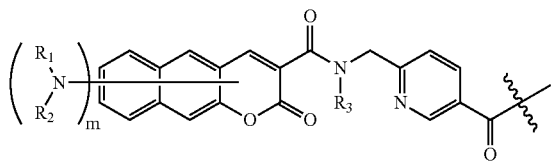

wherein $R_1$, $R_2$, $R_3$ and m are the same as defined in [Chemical Formula 1].

In an exemplary embodiment of the present disclosure, the compound exhibiting blue emission as an internal reference may be a compound represented by [Chemical Formula 4]:

[Chemical Formula 4]

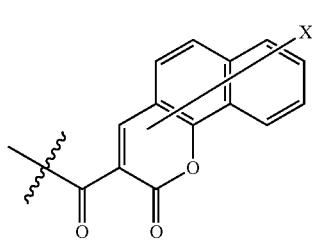

wherein X and n are the same as defined in [Chemical Formula 1].

In another aspect, the present disclosure provides a method for preparing the compound of [Chemical Formula 1] by reacting a compound of [Chemical Formula 5] with a compound of [Chemical Formula 6]:

[Chemical Formula 5]

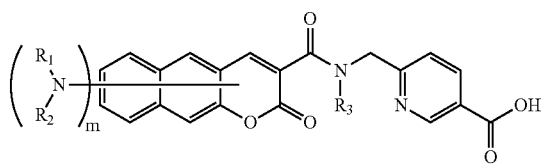

[Chemical Formula 6]

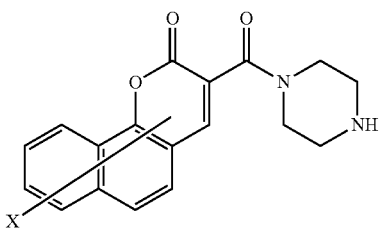

wherein $R_1$, $R_2$, $R_3$, X, m and n are the same as defined in [Chemical Formula 1].

In an exemplary embodiment of the present disclosure, the compound of [Chemical Formula 5] may be prepared by: preparing a compound of [Chemical Formula 9] by reacting a compound of [Chemical Formula 7] with a compound of [Chemical Formula 8]; and replacing the ester group of the [Chemical Formula 9] with a carboxyl group:

[Chemical Formula 7]

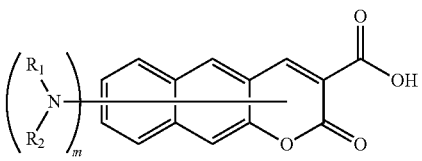

[Chemical Formula 8]

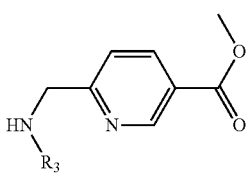

-continued

[Chemical Formula 9]

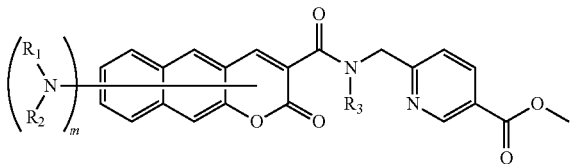

wherein $R_1$, $R_2$, $R_3$, X, m and n are the same as defined in [Chemical Formula 1].

In another exemplary embodiment of the present disclosure, the compound of [Chemical Formula 6] may be prepared by: preparing a compound of [Chemical Formula 11] by reacting a compound of [Chemical Formula 10] with piperazine having one amine group protected by an amine protecting group; and removing the amine protecting group from the compound of [Chemical Formula 11]:

[Chemical Formula 10]

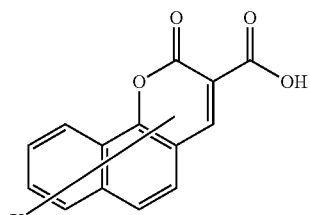

[Chemical Formula 11]

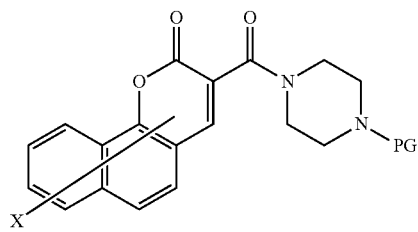

wherein PG is the amine protecting group.

In another aspect, the present disclosure provides a method for quantitatively estimating copper(II) on concentration in vivo using the ratio of emission intensities measured in short wavelength and long wavelength regions as a result of a reaction between the compound of [Chemical Formula 1] and copper(II) on present in vivo.

In an exemplary embodiment of the present disclosure, the distance between the maximum wavelength in the short wavelength region and the minimum wavelength in the long wavelength region may be 70 nm or greater.

In another exemplary embodiment of the present disclosure, the short wavelength region may be 400-480 nm.

In another exemplary embodiment of the present disclosure, the reaction between the compound of [Chemical Formula 1] and the copper(II) ion present in vivo may be conducted at pH 5-7.5.

The present disclosure provides a compound that can be used as a two-photon probe for detecting copper(II) on ($Cu^{2+}$) in vivo with high selectivity and sensitivity with minimum interference from other metal ions and cell membrane-bound probes. The compound according to the present disclosure can monitor intracellular free copper(II) on for a long period of time with a penetration depth of 90-160 μm in living cells and tissues without the problems of mistargeting and pholobleaching.

DETAILED DESCRIPTION OF EMBODIMENTS

Figure 1:
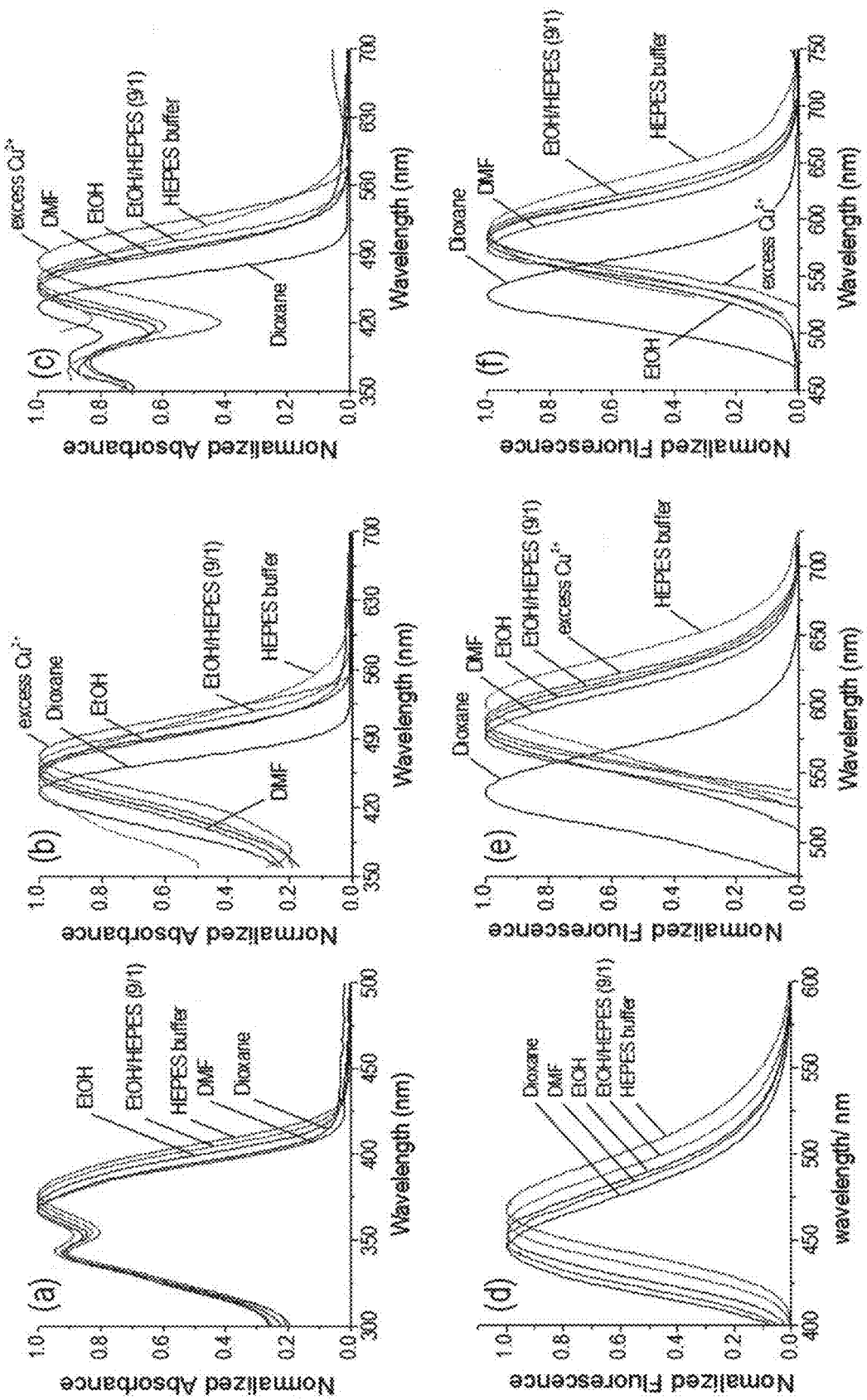
FIG. 1 shows normalized absorption (a-c) and fluorescence (d-f) spectra of a compound of [Chemical Formula 2] (hereinafter, 'ACCu2'), a compound of [Chemical Formula 12] (hereinafter, 'FL') and a compound of [Chemical Formula 13] (hereinafter, 'IR') in 1,4-dioxane, DMF, ethanol, EtOH/HEPES (9:1) and HEPES buffer ([HEPES]=20 mM, pH 7.0).

The present disclosure provides a compound represented by [Chemical Formula 1]:

wherein Me stands for methyl.

The compound of [Chemical Formula 1] according to the present disclosure has very high selectivity for copper(II) on in vivo. As described below, the compound of [Chemical Formula 1] according to the present disclosure has been demonstrated to be capable of selectively binding to copper(II) ion with very high reactivity, as compared to other competing metal ions such as $Na^+$, $K^+$, $Mg^{2+}$, $Ca^{2+}$, $Mn^{2+}$, $Fe^{2+}$, $Co^{2+}$, $N^{2+}$, $Cu^+$, $Zn^{2+}$, $Pd^{2+}$ and $Cd^{2+}$.

Since the compound of [Chemical Formula 1] according to the present disclosure is capable of two-photon absorption and emission, it can be used as a two-photon probe and allows in-vivo imaging based on the two-photon absorption and emission.

The compound of [Chemical Formula 1] according to the present disclosure can effectively detect copper(II) ion at pH 5-7.5.

[Chemical Formula 1]

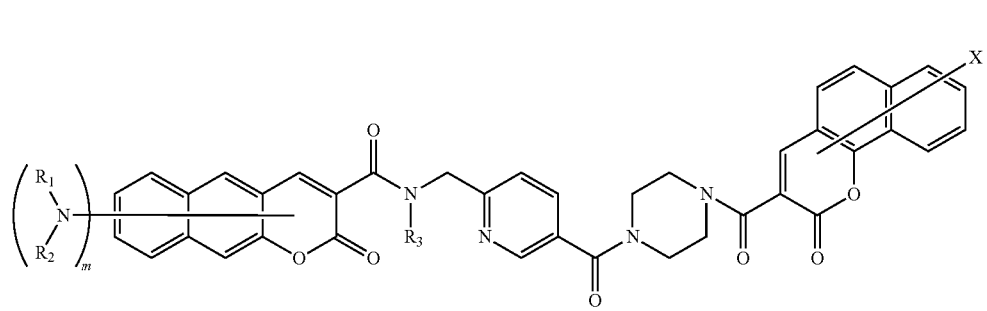

wherein
each of $R_1$, $R_2$ and $R_3$, which are identical or different, is independently hydrogen or $C_1$-$C_{10}$ substituted or unsubstituted alkyl, X is $-OCH_2(CH_2OCH_2)_nCH_2OCH_3$, the substituted alkyl is substituted with a substituent selected from a group consisting of halogen, trifluoromethyl, amino, $C_1$-$C_5$ alkyl, $C_1$-$C_5$ alkoxy, hydroxyl, $C_1$-$C_5$ carboxyl, cyano, phenyl and benzyl, m is an integer from 1 to 3 and
n is an integer from 1 to 6.

In an exemplary embodiment of the present disclosure, the $C_1$-$C_{10}$ substituted or unsubstituted alkyl may he selected from a group consisting of methyl, ethyl, propyl, isopropyl, butyl, sec-butyl, test-butyl, pentyl, hexyl, heptyl, octyl, nonyl and decyl.

In an exemplary embodiment of the present disclosure, the compound represented by [Chemical Formula 1] may be a compound represented by [Chemical Formula 2]:

In order to demonstrate the applicability of the compound of [Chemical Formula 1] according to the present disclosure as an in-vivo imaging agent, detection of copper(II) ion in cultured HeLa cells was conducted. Also, in order to demonstrate whether it can detect copper(II) ion existing deep inside living tissues, TPM images were obtained for rat hippocampal and hypothalamic slices and human colon tissues. As a result, the dye according to the present disclosure has been found to be usefully used to detect copper(II) on in vivo, with excellent detection sensitivity at various depths.

The compound of [Chemical Formula 1] according to the present disclosure may have a penetration depth higher than 90 μm, specifically 90-160 μm, in living cells and tissues.

The present disclosure also provides a method for preparing the compound represented by [Chemical Formula 1] by reacting a compound of [Chemical Formula 5] with a compound of [Chemical Formula 6].

[Chemical Formula 2]

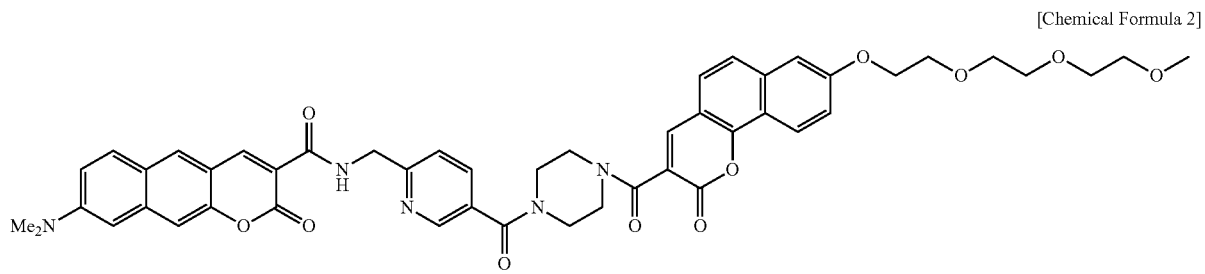 [SMILES: COCCOCCOCCOc1ccc2c(ccc3cc(C(=O)N4CCN(C(=O)c5ccc(CNC(=O)c6cc7cc8ccc(N(C)C)cc8cc7oc6=O)nc5)CC4)c(=O)oc32)c1]

[Chemical Formula 5]

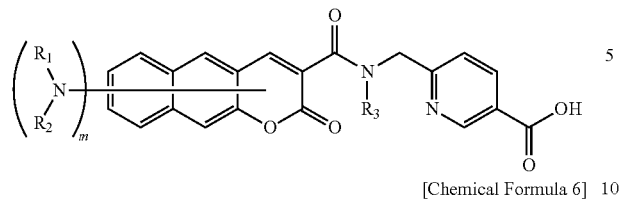

[Chemical Formula 6]

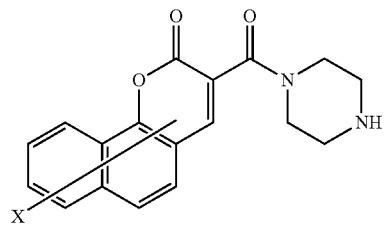

wherein $R_1$, $R_2$, $R_3$, X, m and n are the same as defined in [Chemical Formula 1].

The reaction may be conducted by adding a base to the compound of [Chemical Formula 5] and the compound of [Chemical Formula 6] and stirring the resulting mixture in an organic solvent such as $CH_2Cl_2$. The base may be one or more selected from 1-ethyl-3-(3-dimethylaminopropyl)carbodiimide and 4-dimethylaminopyridine and the reaction may be conducted under inert gas (e.g., argon) flow.

The compound of [Chemical Formula 5] may be specifically a compound of [Chemical Formula 12] and the compound of [Chemical Formula 6] may be specifically a compound of [Chemical Formula 13].

[Chemical Formula 12]

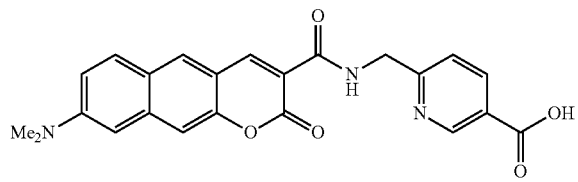

[Chemical Formula 13]

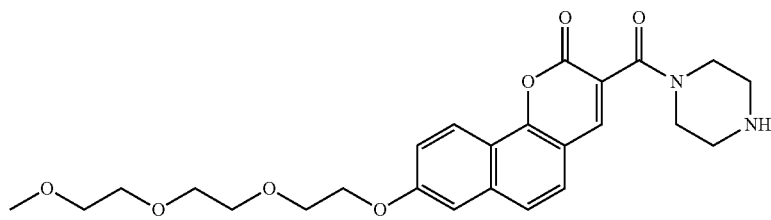

Specifically, the compound of [Chemical Formula 5] may be prepared by: preparing a compound of [Chemical Formula 9] by reacting a compound of [Chemical Formula 7] with a compound of [Chemical Formula 8]; and replacing the ester group of the [Chemical Formula 9] with a carboxyl group:

[Chemical Formula 7]

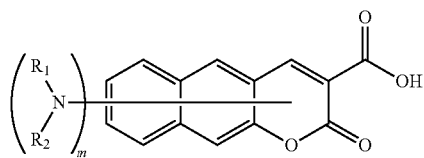

[Chemical Formula 8]

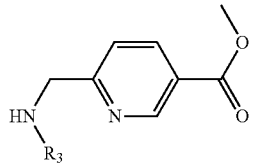

[Chemical Formula 9]

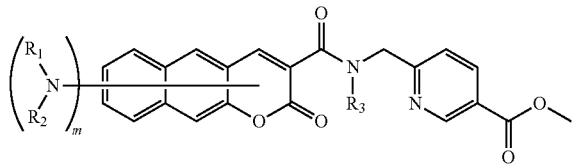

The compound of [Chemical Formula 7] may be specifically a compound of [Chemical Formula 14], the compound of [Chemical Formula 8] may be specifically a compound of [Chemical Formula 15] and the compound of [Chemical Formula 9] may be specifically a compound of [Chemical Formula 16].

[Chemical Formula 14]

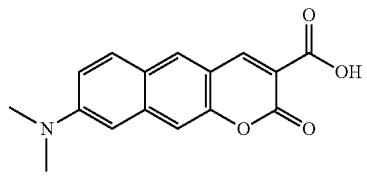

[Chemical Formula 15]

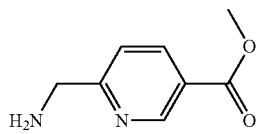

[Chemical Formula 16]

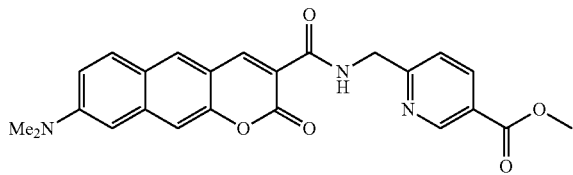

The compound of [Chemical Formula 9] may be prepared by adding a base and stirring the resulting mixture in an organic solvent such as CH$_2$Cl$_2$. The base may be one or more selected from 1,3-dicyclohexylcarbodiimide and 4-dimethylaminopyridine and the reaction may be conducted under inert gas (e.g., argon) flow.

The compound of [Chemical Formula 6] may be prepared by: preparing a compound of [Chemical Formula 11] by reacting a compound of [Chemical Formula 10] with piperazine having one amine group protected by an amine protecting group; and removing the amine protecting group from the compound of [Chemical Formula 11];

[Chemical Formula 10]

[Chemical Formula 11]

wherein

X is the same as defined in [Chemical Formula 1] and

PG is the amine protecting group.

The amine protecting group may be one commonly used to protect an amine group without particular limitation. Specifically, it may be di-tert-butyl pyrocarbonate and the piperazine having one amine group protected by the amine protecting group may be tert-butyl piperazine-1-carbonate.

Specifically, the compound of [Chemical Formula 10] may be a compound of [Chemical Formula 17] and the compound of [Chemical Formula 11] may be a compound of [Chemical Formula 18].

[Chemical Formula 17]

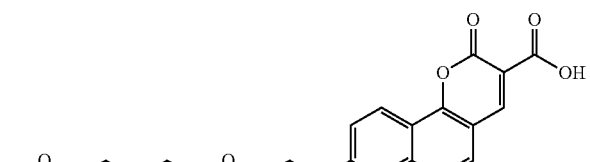

[Chemical Formula 18]

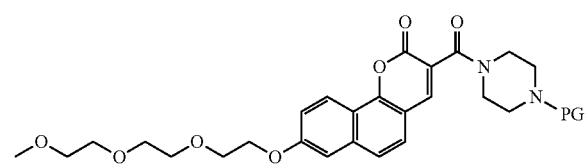

The compound of [Chemical Formula 11] may he prepared by adding a base and stirring the resulting mixture in an organic solvent such as CH$_2$Cl$_2$. The base may he one or more selected from 1,3-dicyclohexylcarbodiirnide and 4-dimethylaminopyridine and the reaction may be conducted under inert gas (e.g., argon) flow.

[Scheme 1] shows an exemplary scheme for preparing the compound represented by [Chemical Formula 2].

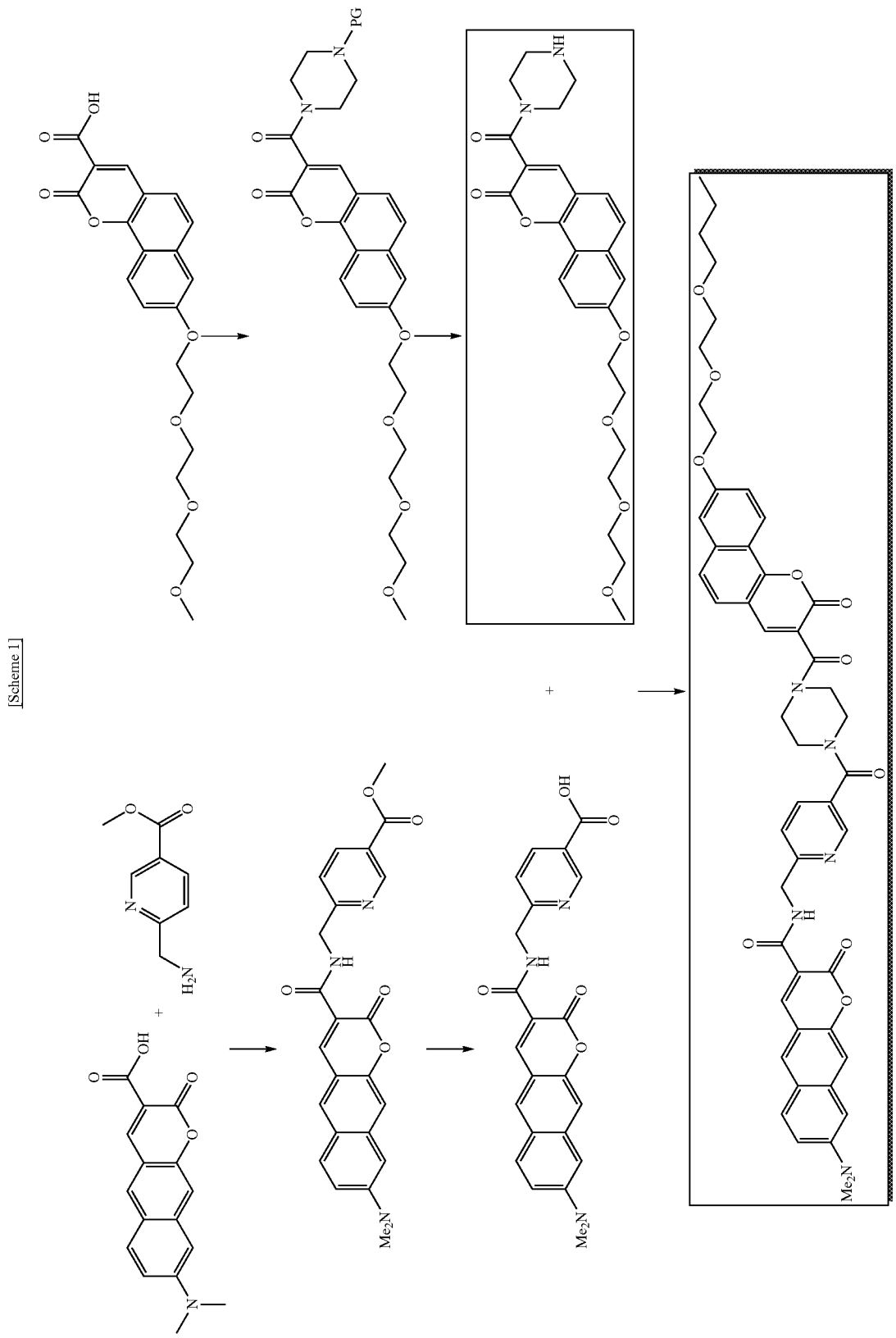
[Scheme 1]

The present disclosure also provides a two-photon probe compound for detecting copper(II) on having a structure in which a compound exhibiting red emission, as a fluorophore and copper(II) on chelator, and a compound exhibiting blue emission, as an internal reference, are bound to both ends of a piperazine group.

The compound exhibiting red emission as a fluorophore and copper(II) on chelator may be a compound represented by [Chemical Formula 3]:

[Chemical Formula 3]

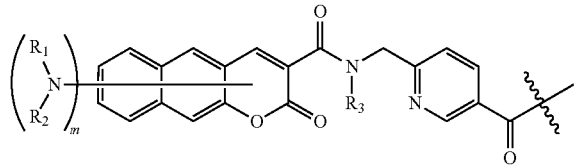

wherein $R_1$, $R_2$, $R_3$ and m are the same as defined in [Chemical Formula 1].

And, the compound exhibiting blue emission as an internal reference may be a compound represented by [Chemical Formula 4]:

[Chemical Formula 4]

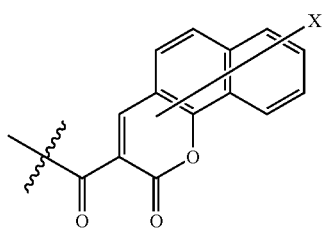

wherein X and n are the same as defined in [Chemical Formula 1].

The compound represented by [Chemical Formula 1] according to the present disclosure may exhibit decreased blue emission intensity in the presence of copper(II) on owing to Forster resonance energy transfer (FRET) resulting from the structure of the compound represented by [Chemical Formula 4]. However, the structure of the compound represented by [Chemical Formula 4] does not directly affect copper(II) ion concentration and the change in copper(II) ion concentration may be detected by monitoring the change in red emission intensity resulting from the structure of the compound represented by [Chemical Formula 3].

Accordingly, in accordance with the present disclosure, copper(II) ion concentration in vivo can be quantitatively estimated by measuring the red/blue emission intensity ratio using the two-photon probe represented by [Chemical Formula 1].

In accordance with the present disclosure, the copper(II) ion concentration in vivo can be quantitatively estimated based on the ratio of emission intensities measured at short wavelength and long wavelength regions as a result of reaction between the compound of [Chemical Formula 1] and the copper(ll) ion present in vivo. The distance between the maximum wavelength in the short wavelength region and the minimum wavelength in the long wavelength region may be 70 nm or greater, specifically 70-150 nm. In an exemplary embodiment of the present disclosure, the short wavelength region may be 380-480 nm and the long wavelength may be 550-700 nm. More specifically, the short wavelength region may be 400-450 nm and the long wavelength may be 550-650 nm.

In accordance with the present disclosure, copper(II) ion concentration in normal, polyp and cancer tissues may be quantitatively estimated using dual-color TPM images obtained using the compound of [Chemical Formula 1] according to the present disclosure by two-photon microscopy (TPM)

Hereinafter, the present disclosure will be described in more detail through examples. However, the following examples are for illustrative purposes only and not intended to limit the scope of this disclosure.

EXAMPLE

Example

Preparation of Compound of [Chemical Formula 2]

1) Preparation of Compound of [Chemical Formula 16]

8-Dimethylamino-2-oxo-2H-benzo[g]chromene-3-carboxylic acid (0.20 g, 0.84 mmol, Chemical Formula 4), 6-(aminornethyl)nicotinate (0.21 g, 1.3 mmol, Chemical Formula 5), 1,3-dicyclohexyl carbodiimide (0.26 g, 1.3 mmol) and 4-dimethylaminopyridine (0.010 g, 0.084 mmol) were dissolved in dichloromethane and stirred for 12 hours under argon flow. Upon completion of reaction, the reaction mixture was filtered and the filtrate was concentrated under reduced pressure. The concentrate was purified by silica gel column chromatography using hexane/EtOAc (1:2) as an eluent to obtain a compound of [Chemical Formula 16], Yield: 0.20 g (64%);

$^1$H NMR (300 MHz, CDCl$_3$): δ 9.20 (1H, d, J=2.0 Hz), 8.96 (1H, s), 8.27 (1H, dd, J=8.8, 2.0 Hz), 8.01 (1H, s), 7.89 (1H, d, J=9.2 Hz), 7.46 (1H, s), 7.43 (1H, d, J=8.8 Hz), 7.16 (1H, dd, J=9.2, 2.5 Hz), 6.81(1H d, J=2.5 Hz), 4.88 (2H, d, J=5.8 Hz), 3.95 (3H, s), 3.16 (6H, s);

$^{13}$C NMR (100 MHz, CDCl$_3$): δ 165.91, 162.94, 162.45, 162.05, 151.50, 150.87, 149.34, 138.67, 138.03, 136.30, 131.28, 130.63, 124.84, 123.92, 121.30, 116.44, 115.03, 114.82, 109.73, 103.97, 52.59, 45.56, 40.51 ppm.

2) Preparation of Compound of [Chemical Formula 12]

The compound of [Chemical Formula 16] (100 mg, 0.23 mmol) was dissolved in a mixture solvent of 5 mL of tetrahydrofuran (THF) and 5 mL, of methanol and KOH (65 mg, 1.2 mmol) dissolved in 5 mL of water was added. The resulting mixture was stirred at room temperature for 3 hours. Upon completion of reaction, the organic solvent was removed from the flask and pH was adjusted to 4-5 with aqueous HCl solution. Subsequently, the residue was extracted with dichloromethane, concentrated and recrystallized in dichloromethane/methanol to obtain a compound of [Chemical Formula 12] as orange crystal. Yield: 50 mg (52%);

$^1$H NMR (300 MHz, DMSO-d$_6$): δ 9.01 (1H, s), 8.96 (1H, s), 8.35 (1H, s), 8.22 (1H, d, J=8.2 Hz), 7,87 (1H, d, J=9.2 Hz). 7.57 (1H, s), 7.48 (1H, d, J=8.2 Hz), 7.28 (1H, d, J=9.2 Hz), 6.96 (1H, s), 4.72 (2H, d, J=5.8 Hz), 3.10 (6H, s) ppm.

3) Preparation of Compound of [Chemical Formula 18]

8-(2-(2-(2-Methoxyethoxy)ethoxy)ethoxy)-2-oxo-2H-benzo[h]chromene-3-carboxylic acid (0.30 g, 0.75 mmol), tert-butyl piperazine-l-carboxylate (0.17 g, 0.89 mmol), 1,3-dicyclohexyl carbodiimide (0.23 g, 1.1 mmol) and 4-dimethylaminopyridine (9.0 mg, 0.075 mmol) were dissolved in dichloromethane and reacted for 12 hours under argon flow. Upon completion of reaction, the reaction mixture was filtered and the filtrate was concentrated under reduced pressure. The resulting concentrate was purified by silica gel column chromatography using hexane/EtOAc (1:2) as an eluent to obtain a compound of [Chemical Formula 18] as colorless oily product. Yield: 0.28 g (65%);

$^1$H NMR (300 MHz, CDCl$_3$): δ 8.44 (1H, d, J=9.3 Hz), 8.08 (1H, s), 7.58 (1H, d, J=8.5 Hz), 7.44 (1H, d, J=8.5 Hz), 7.33 (1H, dd, J=9.3, 2.5 Hz), 7.19 (1H, d, J=2.5 Hz), 4.30 (2H, m), 3.95 (2H, m), 3.78 (4H, m), 3.70 (2H, m), 3.65 (2H, m), 3.54 (6H, m), 3.40 (2H, m), 3.38 (3H, s), 1.47 (9H, s);

$^{13}$C NMR (100 MHz, CDCl$_3$): δ 164.27, 159.93, 158.34, 154.64, 152.41, 145,30, 137.53, 124.61, 124,36, 124.10, 122.45, 120.19, 117.76, 112.47, 107.60, 80.37, 72.04, 71.03, 70.79, 70.70, 69.66, 67,86, 59.10, 47.26, 42.32, 28.45 ppm.

4) Preparation of Compound of [Chemical Formula 13]

The compound of [Chemical Formula 18] (100 mg, 0.19 mmol) was dissolved in dichloromethane (5 mL) and, after adding CF$_3$CO$_2$H (1 mL), stirred for 12 hours under argon flow. Upon completion of reaction, the reaction mixture was concentrated under reduced pressure and then purified by silica gel column chromatography using CHCl$_3$/MeOH (20:1) as an eluent to obtain a compound of [Chemical Formula 13] as colorless oily product. Yield: 67 mg (75%);

$^1$H NMR (500 MHz, acetone-d$_6$): δ 8.30 (2H, d, J=9.3 Hz), 8.11 (1H, s), 7.66 (2H, m), 7.43 (1H, d, J=2.2 Hz), 7.35 (1H, dd, J=9.3, 2.2 Hz), 4.32 (2H, m), 3.92 (2H, m), 3.78 (4H, m), 3.52-3.72 (8H, m), 3.40-3.48 (4H, m), 3.28 (3H, s), 2.78-2.87 (4H, m);

$^{13}$C NMR (125 MHz, acetone-d$_6$): δ 164.55, 159.58, 158.23, 151.72, 145.73, 137.38, 124.92, 123.79, 123.38, 121.05, 119.67, 117.04, 112.43, 107.62, 71.48, 70.39, 70.08, 69.87, 69.28, 67.80, 58.06, 43.50, 43.20 ppm.

5) Preparation of Compound of [Chemical Formula 2]

The compound of [Chemical Formula 12] (50 mg, 0.12 mmol), the compound of [Chemical Formula 13] (67 mg, 0.14 mmol), 1-ethyl-3-(3-dimethylaminopropyl)carbodiimide (28 mg, 0.18 mmol, EDCl) and 4-dimethylaminopyridine (2 mg, 0.012 mmol) were dissolved in dichloromethane and reacted for 12 hours under argon flow. Upon completion of reaction, the reaction mixture was filtered and the filtrate was concentrated under reduced pressure. The resulting concentrate was purified by silica gel column chromatography using ethyl acetate/acetone (3:1) as an eluent to obtain a compound of [Chemical Formula 2] as orange crystal. Yield: 38 mg (36%):

IR (deposit from CH$_2$Cl$_2$ solution on a NaCl plate): 3340 (NH), 1707 (C=O);

$^1$H NMR (500 MHz, CDCl$_3$): δ 9.61 (1H, s), 8.94 (1H, s), 8.68 (1H, s), 8.43 (1H, br), 8.12 (1H, s), 7.99 (1H, s), 7.78 (2H, m), 7.58 (1H, d, J=8.5 Hz), 7.46 (2H, 7.33 (1H, d, J=8.5 Hz), 7.16 (1H, dd, J=9.3, 2.2 Hz), 6.80 (1H, d, J=2.2 Hz), 4.86 (2H, d, J=3.7 Hz), 4.29 (2H, m), 3.95 (2H, m), 3.76-3.80 (4H, m), 3.64-3.72 (8H, m), 3.53-3.57 (4H, m), 3.38 (3H, s), 3.16 (6H, s);

$^{13}$C NMR (100 MHz, CDCl$_3$): δ 168.24, 162.97, 162.48, 160.11, 158.51, 152.69, 151.56, 150.89, 149.42, 147.94, 138.72, 137.74, 136.24, 131.34, 130.67, 129.71. 124.68, 124.60, 124.32, 123.99, 122.00, 121.71, 120.34, 117.86, 116.50, 115.11, 114.88, 113.38, 112.54, 109.80, 107.72, 104.04, 72.13, 71.14, 70.81, 69.75, 67.95, 59.27, 45.45, 43.69, 40.54;

HRMS(FAB$^+$): m/z calculated for [C$_{48}$H$_{47}$N$_5$O$_{11}$ $^+$H$^+$]: 870.3306, found: 870.3350.

Test Examples

Test Example 1

Measurement of Absorption and Fluorescence Spectra

Absorption spectra were recorded using the Hewlett-Packard 8453 diode array spectrophotometer and fluorescence spectra were measured using the Amico-Bowman series 2 luminescence spectrometer a 1 cm standard quartz cell. The fluorescence quantum yield was determined using coumarin 307 and rhodamine B as references according to the literature method (J. N. Demas, G. A. Crosby, *J. Phys. Chem.* 1971, 75, 991).

FIG. 1 shows normalized absorption (a-c) and fluorescence (d-f) spectra of a compound of [Chemical Formula 2] (hereinafter, 'ACCu2'), a compound of [Chemical Formula 12] (hereinafter, 'FL') and a compound of [Chemical Formula 13] (hereinafter, 'IR') in 1,4-dioxane, DMF, ethanol, EtOH/HEPES (9:1) and HEPES buffer ([HEPES]=20 mM, pH 7.0). Excitation wavelength was 420 nm. The solubility of ACCu2 in HEPES buffer ([HEPES]=20 mM, pH 7.0) as determined by the fluorescence method described in the literature (Kim, H. M.; Choo, H. J.; Jung, S. Y.; Ko, Y. G.; Park, W. H.; Jeon, S. J.; Kim, C. H.; Joo, T. H.; Cho, B. R. *Chem Bio Chem* 2007, 8, 553) was 8.0 μM, which was sufficient to stain cells.

The emission spectra of ACCu2 according to the present disclosure showed gradual red shift with the solvent polarity ($E_T^N$) in the following order: 1,4-dioxane<DMF<EtOH<H$_2$O. The large red shift (calculated as 69 nm) in the emission spectra indicates that ACCu2 according to the present disclosure can be usefully used as a polarity probe.

TABLE 1

| Solvent ($E_T^N$)[a] | $\lambda_{max}^{abs}$, nm[b] | | | $\lambda_{max}^{fl}$, nm[b] | | | φ[c] | | |
|---|---|---|---|---|---|---|---|---|---|
| | IR | FL | ACCu2 | IR | FL | ACCu2 | IR | FL | ACCu2 |
| 1,4-Dioxane (0.164) | 367 | 438 | 380/437 | 445 | 536 | 533 | 0.080 | 0.77 | 0.75 |
| DMF (0.386) | 366 | 454 | 371/456 | 448 | 576 | 577 | 0.070 | 0.29 | 0.54 |
| EtOH (0.654) | 372 | 457 | 379/460 | 451 | 582 | 578 | 0.18 | 0.25 | 0.34 |
| EtOH/HEPES (9:1) | 373 | 461 | 379/465 | 460 | 587 | 585 | 0.62 | 0.15 | 0.22 |
| HEPES (1.000)[d] | 375 | 452 | 380/453 | 468 | 590 | 602 | 1.00 | 0.0045 | 0.0028 |

[a]The numbers in the parentheses are normalized empirical parameters of solvent polarity.

[b]$\lambda_{max}$ of one-photon (OP) absorption and emission spectra in nm.

[c]Fluorescence quantum yield. The uncertainty is ± 15%.

[d]HEPES buffer ([HEPES] = 20 mM, pH 7.0), the $E_T^N$ value is for water.

As can be seen from Table 1, it was confirmed that EtOH/HEPES (9:1) is a good model of the intracellular environment and copper(ll) ion can be detected by TPM using ACCu2.

Figure 2:
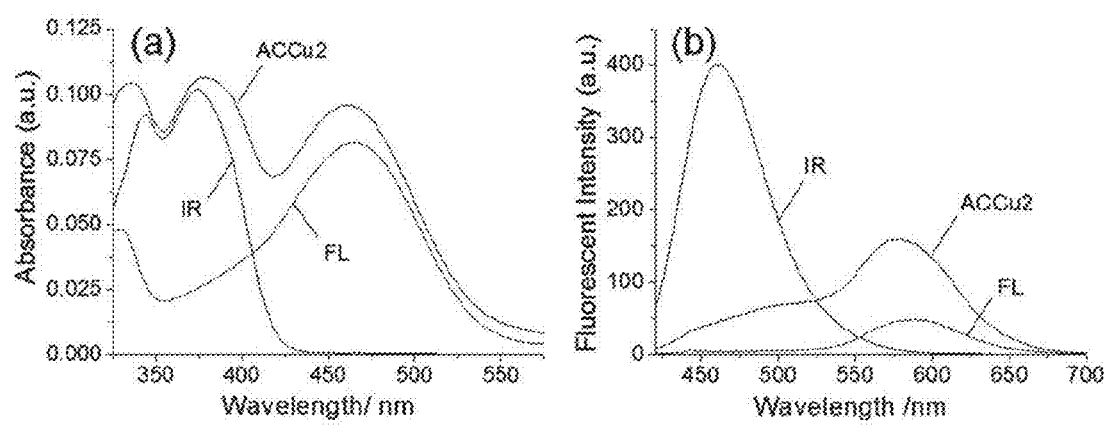
FIG. 2 shows absorption (a) and fluorescence (b) spectra of ACCu2, FL and IR in EtOH/HEPES (9:1, v/v, pH 7.0) when excited at a wavelength of 373 nm.

As can be seen from FIGS. 2(a) and (b), the absorption spectrum of ACCu2 was nearly identical to the sum of those for IR and FL. The emission spectrum of ACCu2 showed two bands that could be attributed to the IR and FL moieties. The area of blue emission (400-450 nm) decreased by 9.2-fold and the area of red emission (550-650 nm) increased by 3.4-fold from those of IR and FL, respectively.

A similar result was observed in a two-photon (TP) mode. As seen from FIG. 3(a), the blue emission was decreased by 13-fold and the red emission was increased by 3.1-fold. To assess the origin of the spectral changes, the energy transfer efficiency (ETE) was calculated using Equation (1). The ETE was 93.4%.

$$ETE = \left(1 - \frac{A_{IR}F_{IR}}{A'_{IR}F'_{IR}}\right) \times 100 \quad \text{Equation (1)}$$

In Equation (1), $A_{IR}$ and $A_{IR}'$ are the absorbances of the IR moiety and IR, respectively, and $F_{IR}$ and $F_{IR}'$ are the emission intensities of the IR moiety and IR, respectively, upon excitation at 373 nm.

The antenna effect in the one-photon (OP) (or TP) mode was 3.0 (or 3.1). The antenna effect was calculated by dividing the area of emission from the FL moiety upon excitation of the IR moiety at 373 nm (or 750 nm in the TP mode) by that collected from the direct excitation of FL at 461 nm (or 880 nm in the IP mode). Therefore, the decrease in the blue emission intensity ($I_{blue}$) can be attributed to the Forster resonance energy transfer (FRET) from IR to FL with an energy transfer efficiency of 93.4%, and the increase in the red emission intensity ($I_{red}$) can be attributed to the antenna effect.

Figure 4:
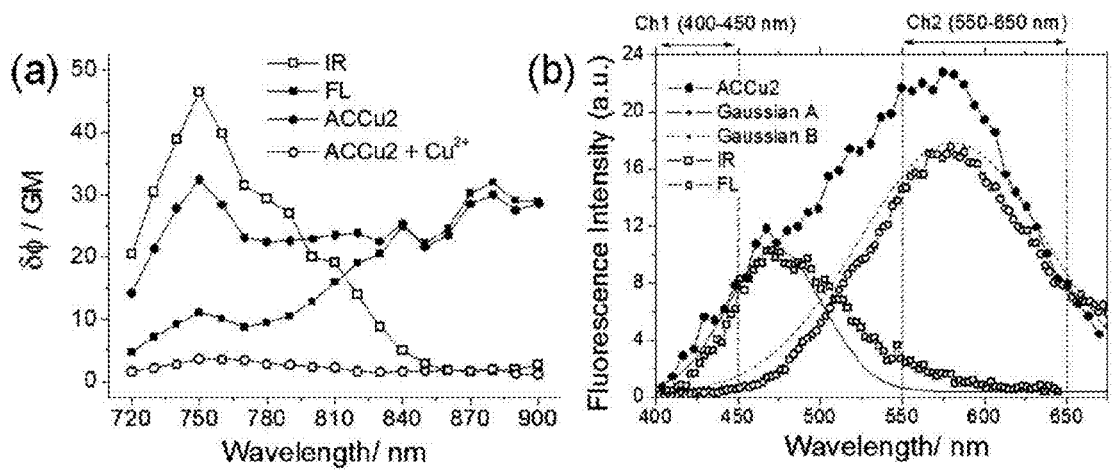
FIG. 4(a) shows two-photon fluorescence spectra of ACCu2, FL and IR in EtOH/HEPES (9:1, v/v, pH 7.0) in the presence of copper(II) ion.
FIG. 4(b) shows two-photon excited fluorescence (TPEF) spectra of HeLa cells containing ACCu2, FL and IR when excited at a wavelength of 740 nm. The TPEF spectra of the ACCu2-labeled HeLa cells were dissected into two Gaussian functions centered at 470 and 582 nm, respectively.

Referring to FIG. 4(a), the $\Phi\delta_{max}$ value of ACCu2 in EtOH/HEPES (9/1 v/v, pH 7.0) buffer was 32 GM at 880 nm, while those for FL and IR were 32 GM at 880 nm and 46 GM at 750 nm. The lower $\Phi\delta_{max}$ value of ACCu2 at 750 nm than that of IR is because of decreased fluorescence resonance energy transfer (FRET) from IR to FL and it allows to obtain bright TPM images of cells and tissues labeled with ACCu2.

Referring to FIG. 4(b), upon 750 nm TP excitation in scanning lambda mode, HeLa cells labeled with ACCu2 showed a broad spectrum which could be dissected into two Gaussian functions with emission maxima at 470 nm (solid curve) and 582 nm (dotted curve). The two curves were similar to the TPEF spectra of HeLa cells labeled with FL and IR. And, the OP-excited fluorescence (OPEF) spectra of FL and IR measured in EtOH/HEPES (9/1 v/v, pH=7.0) (see Table 1 and FIG. 1) confirmed that this solvent is a good model of the intracellular environment. Furthermore, the TPEF intensities of FL and IR could be detected with minimum interference from each other using detection windows of channell (400-450 nm, ch1) and channel 2 (550-650 nm, Ch2), respectively, as seen from FIG. 3(b) and FIG. 4(b).

Test Example 2

Fluorescence Titration

To determine the $K_d$ value for the two-photon process, TPEF spectra were recorded using the DM IRE2 microscope (Leica) excited by a mode-locked titanium-sapphire laser source (Coherent Chameleon, 90 MHz, 200 fs) set at a wavelength of 750 nm.

Figure 3:
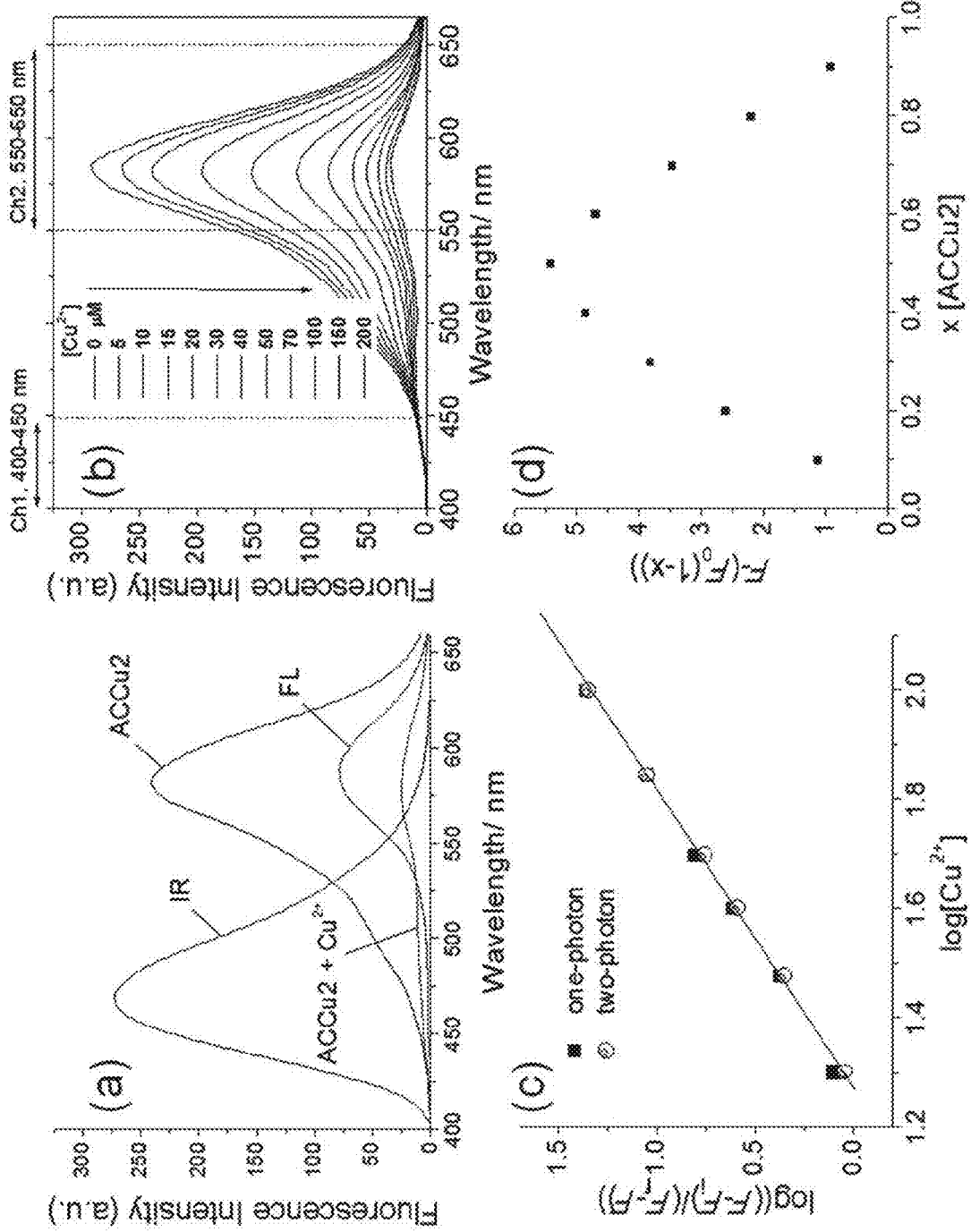
FIG. 3(a) shows fluorescence spectra of ACCu2, FL and IR in EtOH/HEPES (9:1, v/v, pH 7.0) when excited by TP at a wavelength of 373 nm.
FIG. 3(b) shows two-photon excited fluorescence intensities of ACCu2 (3 μM) in the presence of free copper(II) ion at various concentrations (0-200 μM).
FIG. 3(c) shows Hill plots of ACCu2 (3 μM) in the presence of free copper(II) ion at various concentrations (0-200 μM).
FIG. 3(d) shows a working curve for determining the stoichiometry of ACCu2-$Cu^{2+}$ in EtOH/HEPES (9:1, v/v, pH 7.0).

Referring to FIG. 3(b), when small increments of copper (II) ion were added to ACCu2 in EtOH/HEPES (9/1 viv, pH=7.0), the TPEF intensity at the channel 2 ($I_{red}$) decreased gradually without any appreciable change at the channel 1 ($I_{blue}$). A similar result was observed in the TP mode.

The dissociation constant ($K_d$) can be calculated using Equation (2):

$$I - I_{initial} = \frac{[CU^{2+}](I_{final} - I_{initial})}{K_d + [C^{2+}]} \quad \text{Equation (2)}$$

wherein I is the fluorescence intensity, $I_{final}$ is the fluorescence intensity for the $CU^{2+}$-ACCu2 complex and $I_{initial}$ is the fluorescence intensity for ACCu2.

The dissociation constants ($K_d^{OP}$ and $K_d^{TP}$) of ACCu2 for the OP and TP processes can be calculated from the fluorescence titration curves shown in FIG. 3(b). As seen from FIG. 3(c), the Hill plots for copper(II) on measured by the OP and TP processes showed good linearity with a slope of 1.0. Also, as seen from FIG. 3(d), the Job plot exhibited a maximum at a molar fraction of 0.20. These indicate 1:1 complexation between the probe and the cation. The calculated dissociation constant values $K_d^{OP}$ and $K_d^{TP}$ for copper(II) on were 21±3 µM and 22±4 µM, respectively.

Figure 5:
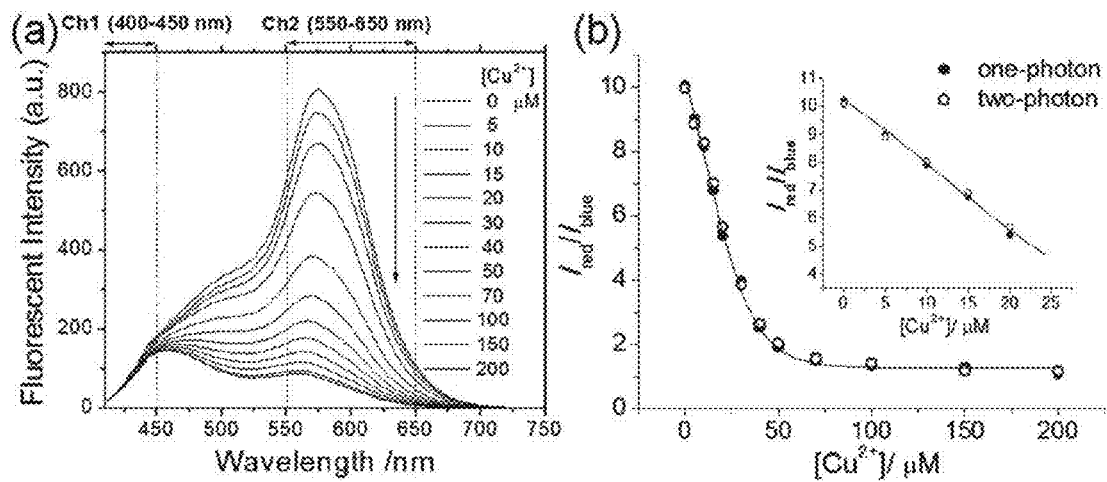
FIG. 5(a) shows change in the fluorescence intensity of ACCu2 depending on copper(II) ion concentration as measured by a one-photon method.
FIG. 5(b) shows titration curves depending on copper(II) ion concentration as measured by one-photon and two-photon methods.

Referring to FIG. 5(a), the fluorescence intensities of ACCu2 according to the present disclosure measured by the OP (one-photon) and TP (two-photon) processes decreased by 10-fold in the presence of 200 µM of copper(II) ion. In addition, Referring to FIG. 5(b), the plot of $I_{red}/I_{blue}$ showed good linearity in the copper(II) ion concentration range of 0-0.25 µM. This means that quantitative measurement of copper(II) ion is possible in this concentration range. Moreover, the $I_{red}/I_{blue}$ ratios determined in the two-photon mode were well fitted by the titration curve obtained in the one-photon mode. These results suggest that ACCu2 according to the present disclosure can be effectively used to quantitatively estimate copper(Il) ion through dual-color TPM imaging. The detection limit for copper ion using ACCu2 by TPM was found to be 0.84 µM.

The two-photon cross section (δ) was determined by the fetosecond (fs) fluorescence measurement technique described in the literature (S. K. Lee, W. J. Yang, J. J. Choi, C. H. Kim, S.-J. Jeon, B. R. Cho, Org. Lett 2005, 7, 323-326.), ACCu2 was dissolved in 20 mM HEPES buffer (pH 7.0) to a concentration of $3.0 \times 10^{-6}$ M and then two-photon induced fluorescence intensity was measured at 740-940 nm using rhodamine 6G as a reference, whose two-photon property has been well characterized. The intensities of two-photon induced fluorescence of the reference and the sample were determined at the same excitation wavelength.

The two-photon cross section can be calculated from equation (3).

$$\delta = \delta_r(S_s\Phi_r\Phi_r c_r)/(S_r\Phi_s\Phi_s c_s) \quad \text{Equation (3)}$$

wherein s and r stand for the sample, i.e., ACCu2, and the reference, respectively. S denotes the intensity of the signal collected using a CCD detector, Φ is the fluorescence quantum yield, Φ is the overall fluorescence collection efficiency of the experimental apparatus, c is the number density of molecules in solution, and $\delta_r$ is the two-photon cross section of the reference molecule.

Test Example 3

Selectivity of ACCu2 for Copper(II) Ion

Figure 6:
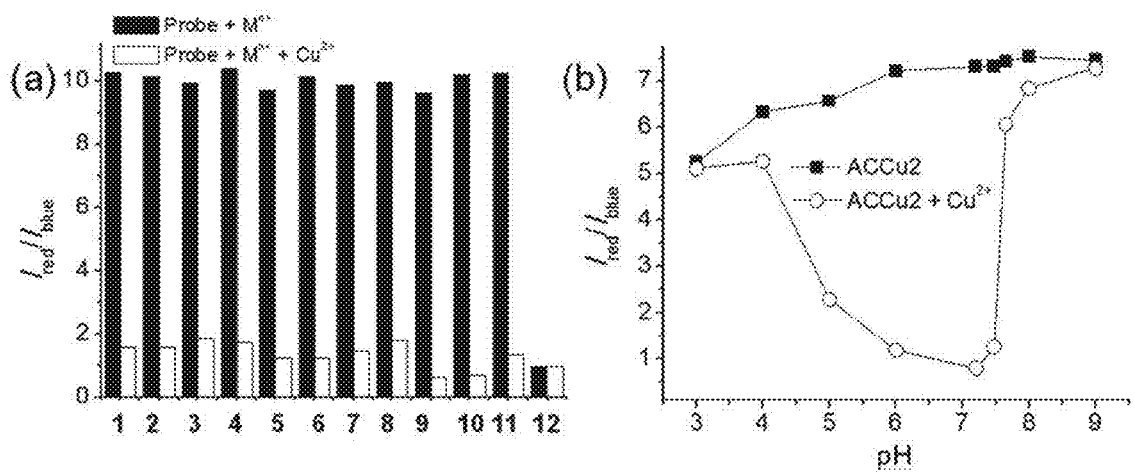
FIG. 6(a) shows fluorescence intensity ratios ($I_{red}/I_{blue}$) of ACCu2 as a measure of reactivity for copper(II) ion compared with competing metal ions (1: $Na^+$; 2: $K^+$; 3: $Mg^{2+}$; 4: $Ca^{2+}$; 5: $Mn^{2+}$; 6: $Fe^{2+}$; 7: $Co^{2+}$; 8: $Ni^{2+}$; 9: $Zn^{2+}$; 10: $Pd^{2+}$; 11: $Cd^{2+}$; 12: $Cu^{2+}$.
FIG. 6(b) shows the effect of pH on the fluorescence intensity ratio ($I_{red}/I_{blue}$) of ACCu2 in the absence or presence of copper(II) ion.

FIG. 6(a) shows fluorescence intensity ratios ($I_{red}/I_{blue}$) of ACCu2 (3 µM) as a measure of reactivity for copper(II) ion compared with competing metal ions. The black bars show the result obtained in the presence of alkali metal and alkaline earth metal ions $Na^+$, $K^+$, $Ca^{2+}$ and $Mg^{2+}$ (1 mM) and transition metal ions $Mn^{2+}$, $Fe^{2+}$, $Co^{2+}$, $Ni^{2+}$, $Zn^{2+}$, $Pd^{2+}$, $Cd^{2+}$ and $Cu^{2+}$ (500 µM) in EtOH/HEPES (9/1 v/v, pH 7.0), and the white bars show the result obtained after further addition of 200 µM $Cu^{2+}$.

It can be seen that the selectivity of ACCu2 for $Cu^{2+}$ is uninterrupted in the presence of the alkali metal, alkaline earth metal or transition metal ions. Accordingly, it was confirmed that ACCu2 according to the present disclosure can selectively detect copper(II) ion in cells.

Test Example 4 pH Dependence

FIG. 6(b) shows a result of measuring the $I_{red}/I_{blue}$ ratio of 3 µM ACCu2 in the in the presence of 0 (black squares) and 200 µM (white circles) copper(II) on in HEPES buffer (EtOH/HEPES; 9/1 v/v, pH 7.0). The excitation wavelength was 365 nm. Referring to FIG. 6(b), the $I_{red}/I_{blue}$ ratio showed a minimum at pH 6-7. The increase in the $I_{red}/I_{blue}$ ratio at pH<6 can be attributed to the protonation of the nitrogen atom in the pyridine moiety as shown in [Chemical Formula 19]. On the other hand, the increase in the $I_{red}/I_{blue}$ ratio at pH>7.0 can be attributed to the decreased copper(II) ion concentration due to the formation of $Cu(OH)_2$. This outcome is different from that reported for the existing one-photon probe.

[Chemical Formula 19]

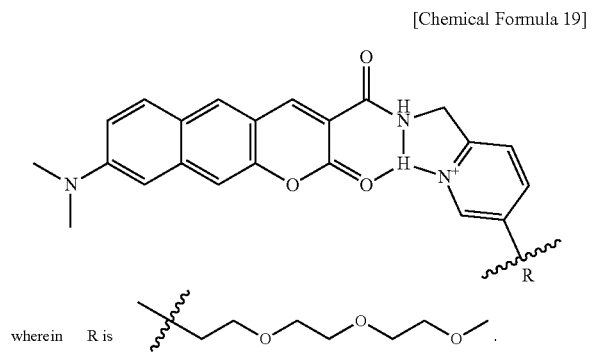

wherein R is

Test Example 5

Quantitative Estimation of Copper(II) Ion Concentration in HeLa Cells

1) Two-Photon Microscopy

In order to investigate the utility of ACCu2 in living cells, TPM images of ACCu2-labeled HeLa cells and tissues were obtained using spectral confocal and multiphoton microscopes (Leica TCS SP2) with ×100 (NA=1.30 OIL) and ×40 (NA=0.75 DRY) objective lenses.

The TPM images were obtained with the DM IRE2 microscope (Leica) by exciting the probes with a mode-locked titanium-sapphire laser source (Coherent Chameleon, 90 MHz, 200 fs) set at a wavelength of 780 nm and an output power of 1305 mW. To obtain images at 400-650 nm, internal PMTs were used to collect signals in 8-bit unsigned 512×512 pixels at a scan rate of 400 Hz.

2) Cell Culture

HeLa human cervical carcinoma cells were acquired from the ATCC (Manassas, Va., USA). The cells were cultured in DMEM (WelGene, Inc., Seoul, Korea) supplemented with heat-inactivated 10% FBS (WelGene), penicillin (100 units/mL) and streptomycin (100 mg/mL), All the cell lines were maintained in a humidified atmosphere of 5% $CO_2$ and 95% air at 37° C. Two days before imaging, the cells were moved and plated onto glass-bottomed dishes (MatTek), For labeling, the growth medium was removed and replaced with FBS-free DMEM. The cells were incubated with 3 µM ACCu2 for 20 minutes at 37° C., washed 3 times with FBS-free DMEM and imaged.

3) Cell Viability

Figure 7:
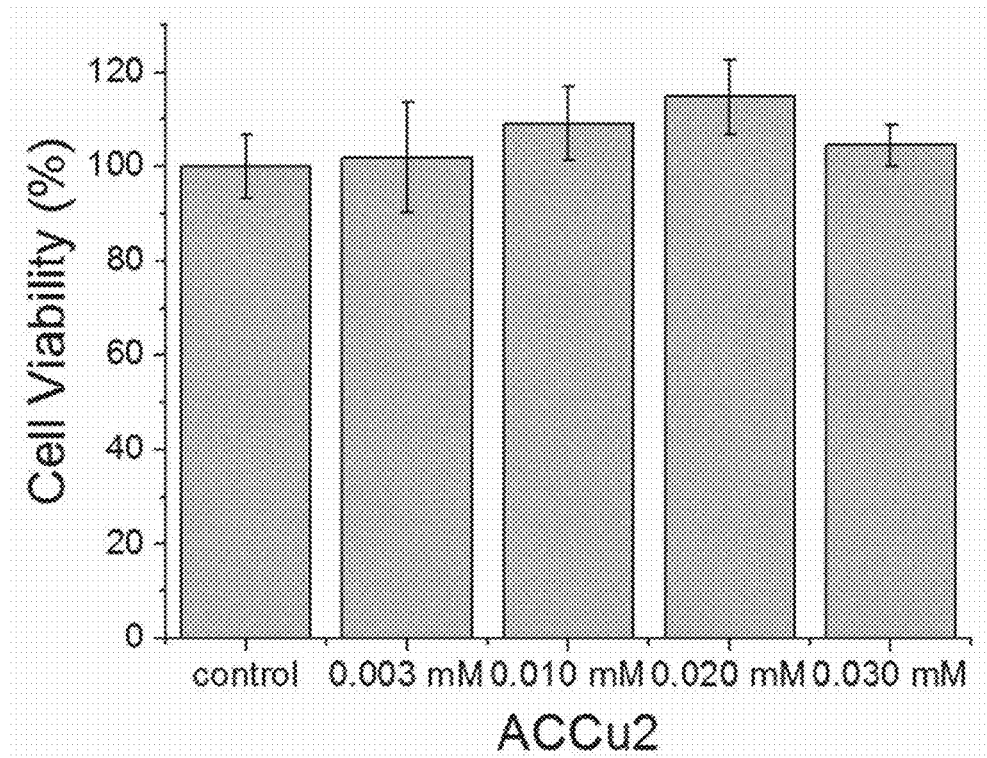
FIG. 7 shows the viability of HeLa cells in the presence of ACCu2 at various concentrations as measured by using the CCK-8 kit (Cell Counting Kit-8, Dojindo, Japan) according to an exemplary embodiment of the present disclosure.
Figure 8:
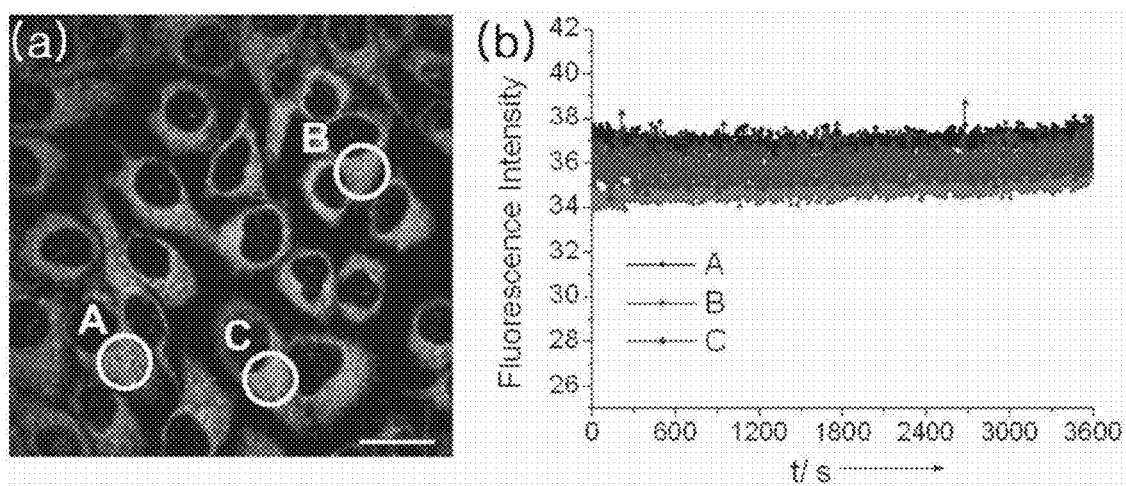
FIG. 8(a) shows TPM images of ACCu2 (3 μM)-labeled HeLa cells collected at 400-650 nm according to an exemplary embodiment of the present disclosure.
FIG. 8(b) shows the relative TPEF intensity as a function of time.

The viability of HeLa cells with the ACCu2 concentration was measured under the incubation condition using the CCK-8 kit (Cell Counting Kit-8, Dojindo, Japan) (FIG. 7). As seen from FIG. 7, ACCu2 according to the present disclosure did not affect the viability of HeLa cells. Accordingly, it can be seen that the copper(II) ion concentration in living cells can be measured with minimum interference from cytotoxicity.

4) Photostability

The photostability of ACCu2 was determined by monitoring the change in TP excited fluorescence (TPEF) intensity from ACCu2 (3 M)-labeled HeLa cells. The TPEF intensity remained nearly the same after continuous radiation of fs-pulses for 60 minutes. This confirms that ACCu2 according to the present disclosure has high photostability and can measure the copper(II) ion concentration in living cells with minimum interference.

5) Quantitative Estimation of Copper(II) Ion Concentration in Cells

To investigate the utility of ACCu2 in vivo, the TPEF intensity from ACCu2 (3 mM)-labeled HeLa cells was monitored at channel 1 (400-450 nm) and channel 2 (550-650 nm. FIG. 9(a) shows a TPM image of obtained using the channel 1 (400-450 nm, $I_{blue}$) detection window and FIG. 9(b)-(d) show TPM images obtained using the channel 2 (550-650 nm, $I_{red}$) detection window, FIG. 9(b) shows the TPM image of the fluorescence-labeled HeLa cells before addition of copper(II) ion and FIG. 9(c) shows the TPM images after addition of 200 µM copper(II) ion and 100 µM PDTC. FIG. 9(d) shows the TPM image after addition of 200 µM copper(II) ion, 100 µM PDTC and 100 µM EDTA (scale bar: 30 µm).

Figure 9:
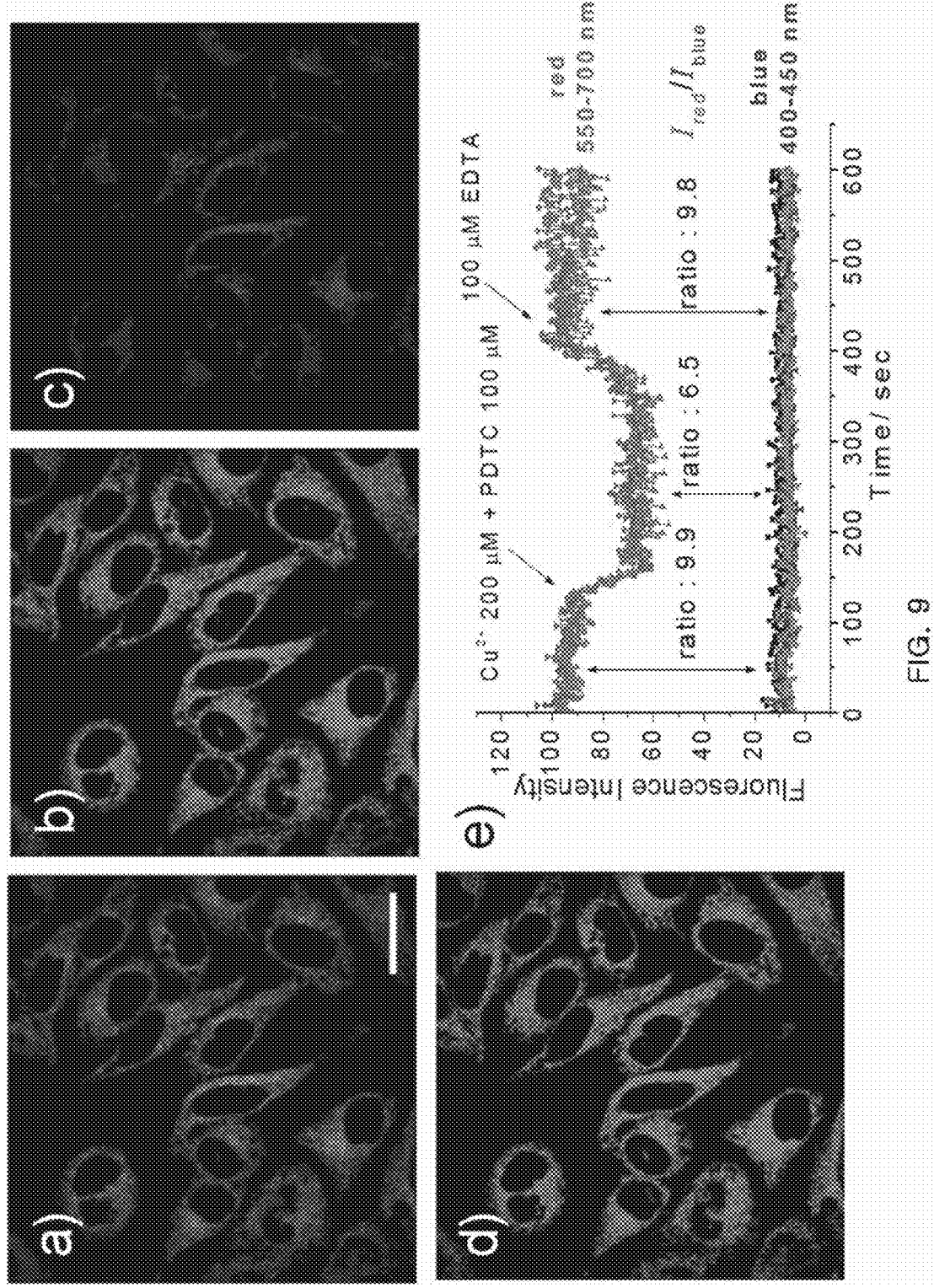
FIG. 9 shows TPM images of ACCu2 (3 μM)-labeled HeLa cells obtained by 750 nm excitation according to an exemplary embodiment of the present disclosure. (a) shows a TPM image of obtained using a channel 1 (400-450 nm, $I_{blue}$) detection window and (b)-(d) show TPM images obtained using a channel 2 (550-650 nm, $I_{red}$) detection window. (e) shows the change in TPEF intensity of ACCu2 (3 μM)-labeled HeLa cells as a function of time after addition of copper(II) ion, PDTC and EDTA.

Referring to FIG. 9, the TPM images of the ACCu2-labeled HeLa cells were very bright because of the good cell permeability and significant TP action cross section. Ratiometric images were constructed from the TPEF intensities collected in the two channels (FIG. 9(a)-(c)). The $I_{red}/I_{blue}$ ratio for the ACCu2-labeled HeLa cells was measured as 9.9±0.8 (FIG. 9(d)). The ratio decreased to 6.5 upon addition of copper(II) ion (200 µM) and pyrrolidine dithiocarbamate (PDTC, 100 µM) due to accumulation of copper(II) ion inside the cells, and increased to 9.8 upon treatment with ethylenediaminetetraacetic acid (EDTA, 100 µM), a membrane-permeable metal on chelator that effectively removes copper(II) ion.

Since $I_{blue}$ remains constant, ACCu2 according to the present disclosure can measure the $I_{red}/I_{blue}$ ratio more accurately than the existing probe which requires the measurements of the changes in both $I_{red}$ and $I_{blue}$. The free copper(II) ion concentration was calculated as 0.0±0.7 µM (FIG. 9(a)), 15±2 µM (FIG. 9(b)) and 0.0±1.9 µM (FIG. 9(c)) from the $I_{red}/I_{blue}$ ratio and the titration curve shown in FIG. 5(b). Because the intracellular free copper(I) ion was less than one per cell, this result confirms the low cell permeability of copper(II) ion.

Test Example 6

Quantitative Estimation of Copper(II) Ion Concentration in Rat Brain Tissue

Slices were prepared from the hippocampi and hypothalami of 2-day-old Sprague-Dawley (SD) rats. Coronal slices were cut into 400 μm thickness using a vibrating-blade microtome in artificial cerebrospinal fluid (ACSF; 138.6 mM NaCl, 3.5 mM KCl, 21 mM NaHCO$_3$, 0.6 mM NaH$_2$PO$_4$, 9.9 mM D-glucose, 1 mM CaCl$_2$ and 3 mM MgCl$_2$). The slices were incubated with 20 μM ACCu2 in ACSF bubbled with 95% O$_2$ and 5% CO$_2$ for 30 minutes at 37° C. The slices were e then washed 3 times with ACSF, transferred to glass-bottomed dishes (MatTek) and observed with spectral confocal and rnultiphoton microscopy.

Figure 10:
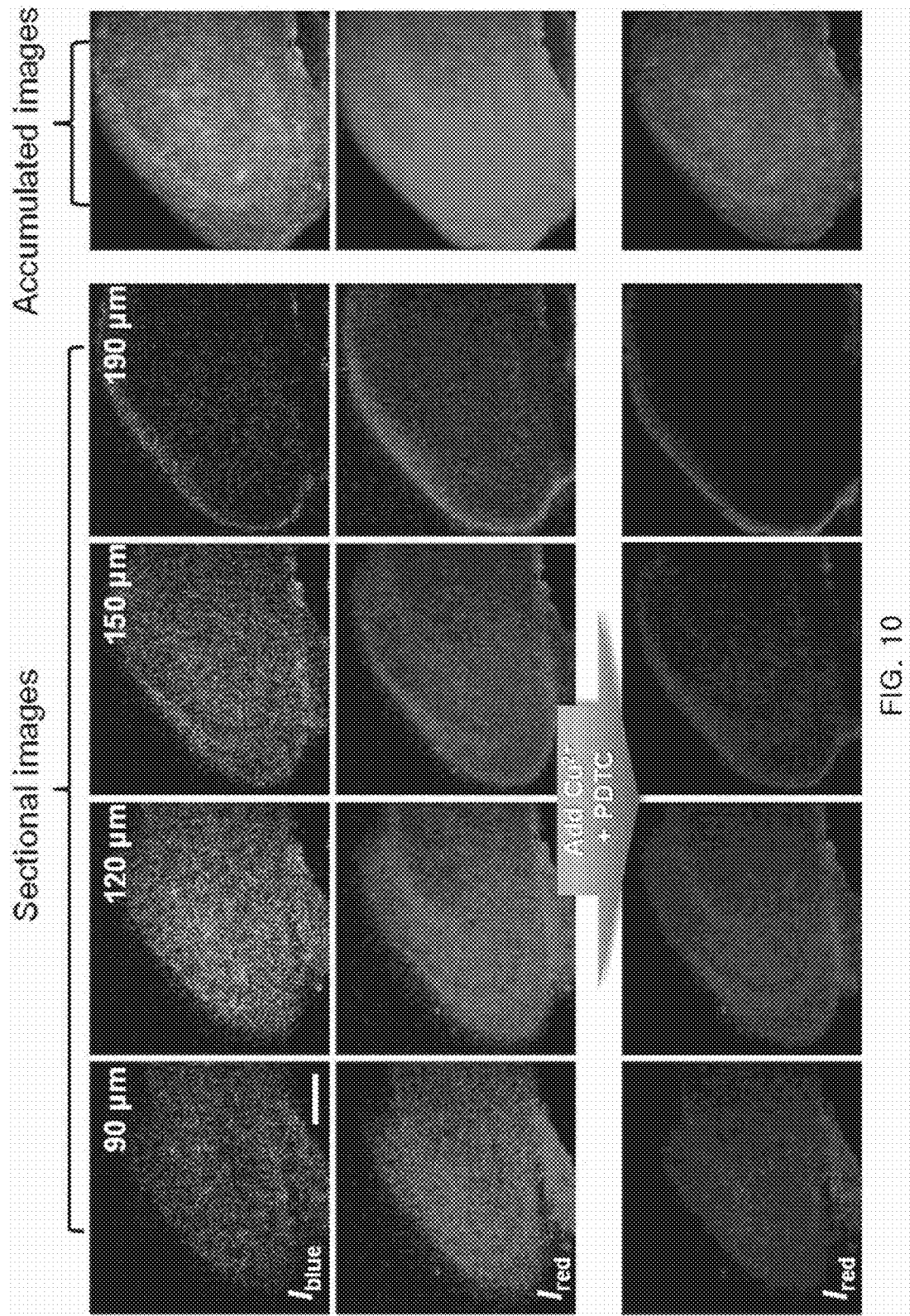
FIG. 10 shows TPM images of a rat hippocampal slice treated with ACCu2 (20 μM) according to an exemplary embodiment of the present disclosure. The images were acquired using 750 nm excitation and detection windows at channel 1 (400-450 nm, $I_{blue}$) and channel 2 (550-650 nm, $I_{red}$) (scale bar: 300 μm).

Because the structure of the brain tissue is heterogeneous, TPM images were acquired at depths of 90-190 μm to visualize the overall copper(II) on distribution. The result is shown in FIG. 10.

The $I_{red}/I_{blue}$ ratio for the ACCu2-labeled rat brain tissue was 9.9±0.5, which corresponded to 0.0±1.1 μM free copper (II) ion. Because the copper ion in the brain tissue is expected to be transferred from the cerebrospinal fluid (CSF), where the free copper ion is estimated to be 2.5 μg/L. (0.04 μM), the near-zero concentration seems reasonable.

The $I_{red}/I_{blue}$ ratio for the ACCu2-labeled rat brain tissue decreased to 6.8±0.6 upon treatment with copper(II) ion (500 μM) and PDTC (200 μM), which corresponded to 14±1.5 μM free copper ion.

Test Example 7

Quantitative Estimation of Copper(II) Ion Concentration in Human Colon Tissue

Colon slices were obtained from outpatients who underwent elective colonoscopies at the Korea University Medical Center Anam Hospital. The volunteers were recruited to participate in the experiment, which was approved by the hospital ethics committee, and all the participating patients provided informed consents. The patients who had known or suspected bleeding disorders, an international normalized ratio of prothrombin time exceeding 1.4 a platelet count of <100,000 or who had taken aspirin within the previous 5 days were excluded.

During the colonoscopy examination, tissues were obtained from malignant lesions, adenomas and normal mucosa by biopsy forceps. Normal colon mucosal and adenoma or adenocarcinoma tissues were collected from the same patient. Standard biopsy forceps (Olympus Medical Systems Corporation, Tokyo, Japan) were used to obtain paired mucosal pinch biopsy specimens from the colon. 28, 10 and 6 tissue samples were acquired from normal, polyp and cancer tissues, respectively. The tissues were placed in sterile specimen bottles containing PBS. Half of the normal tissue samples were treated with EDTA (1 M) for 40 minutes. Then, the tissue samples were stained with 20 μM ACCu2 in artificial spinal fluid for 1-2 hours at 37.8° C. and then imaged.

Figure 11:
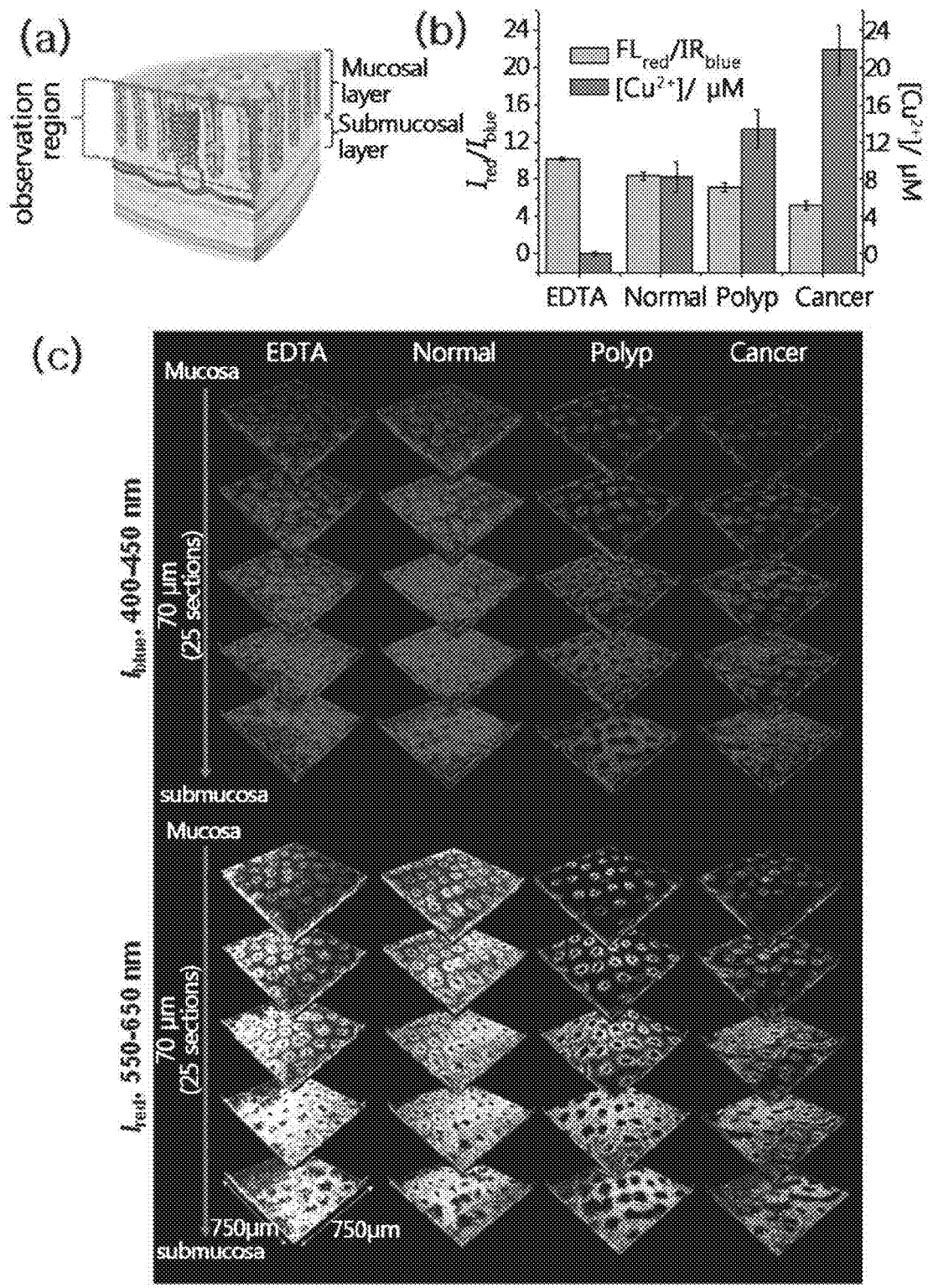
FIG. 11(a) schematically shows the mucosa, muscularis mucosae and submucosa layers.
FIG. 11(b) shows $I_{red}/I_{blue}$ ratios (left, light gray) and $Cu^{2+}$ concentrations (right, dark gray) of EDTA-treated normal, normal, polyp and cancer tissues of the colon.
FIG. 11(c) shows TPM images of EDTA-treated normal, normal, polyp and cancer tissues of the colon obtained according to an exemplary embodiment of the present disclosure. The images were acquired using detection windows at channel 1 (400-450 nm, $I_{blue}$) and channel 2 (550-650 nm, $I_{red}$).

As a result, clinical important images were obtained at depths of 90-190 μm in the mucosal and submucosal layers, as shown in FIG. 11(a).

Figure 12:
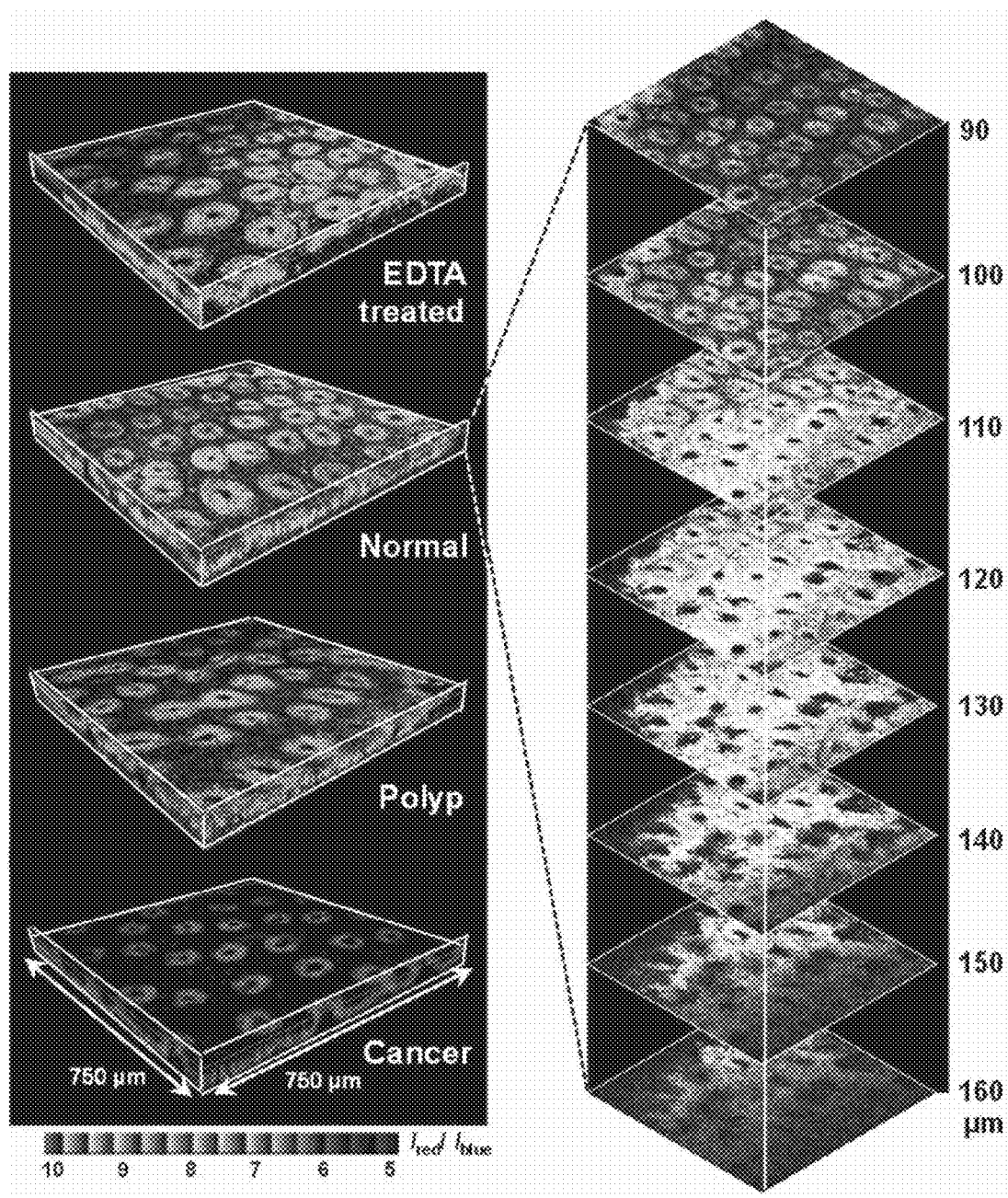
FIG. 12 shows 3-dimensional ratiometric TPM images of EDTA-treated normal, normal, polyp and cancer tissues of the colon at a depth of 90-160 μm.

FIG. 11(c) and FIG. 12 show the ratiometric TPM images of the tissues labeled with ACCu2 according to the present disclosure. FIG. 11(c) shows the sectional images of the distribution of copper(II) ion at different depths of the EDTA-treated normal, normal, polyp and cancer tissues, and FIG. 12 shows the 3-dimensional ratiometric TPM image. As seen from FIG. 11(b), the average $I_{red}/I_{blue}$ ratios in the EDTA-treated normal, normal, polyp and cancer tissues were 10.0±0.3, 8.3±0.4, 7.2±0.5 and 5.2±0.6, which corresponded to copper(II) ion concentrations of 0.0±0.1, 8.2±0.3, 13±2 and 22±3 μM, respectively.

This result suggests that ACCu2 according to the present disclosure may be useful for the early diagnosis and quantitative estimation of colon cancer.

What is claimed is:

1. A compound represented by [Chemical Formula 1]:

[Chemical Formula 1]

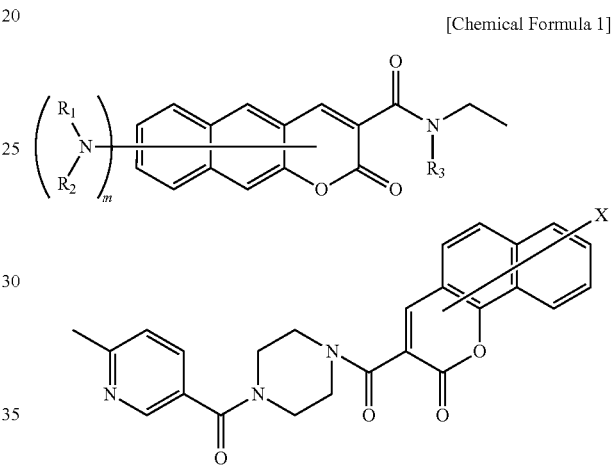

wherein
each of $R_1$, $R_2$ and $R_3$, which are identical or different, is independently hydrogen or $C_1$-$C_{10}$ substituted or unsubstituted alkyl,
X is —OCH$_2$(CH$_2$OCH$_2$)$_n$CH$_2$OCH$_3$,
the substituted alkyl is substituted with a substituent selected from a group consisting of halogen, trifluoromethyl, amino, $C_1$-$C_5$ alkyl, $C_1$-$C_5$ alkoxy, hydroxyl, $C_1$-$C_5$ carboxyl, cyano, phenyl and benzyl,
m is an integer from 1 to 3 and
n is an integer from 1 to 6.

2. The compound according to claim 1, wherein the compound represented by [Chemical Formula 1] is a compound represented by [Chemical Formula 2]:

[Chemical Formula 2]

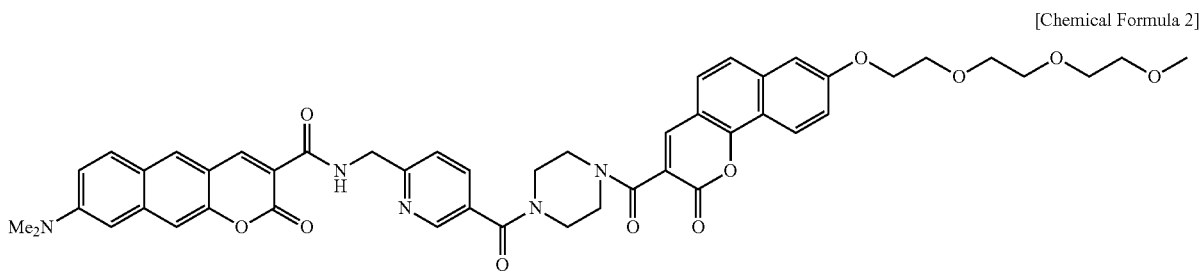

wherein Me stands for methyl.

3. A two-photon probe compound for detecting copper(II) ion having a structure represented by [Chemical Formula 1]:

[Chemical Formula 1]

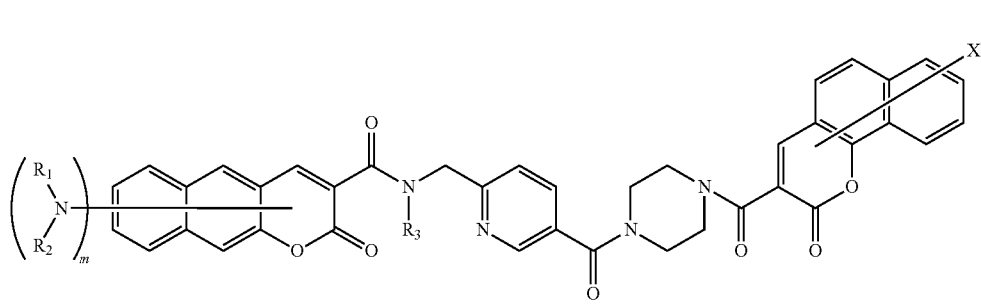

wherein
each of $R_1$, $R_2$ and $R_3$, which are identical or different, is independently hydrogen or $C_1$-$C_{10}$ substituted or unsubstituted alkyl,
X is —$OCH_2(CH_2OCH_2)_nCH_2OCH_3$,
the substituted alkyl is substituted with a substituent selected from a group consisting of halogen, trifluoromethyl amino, $C_1$-$C_5$ alkyl, $C_1$-$C_5$ alkoxy, hydroxyl, $C_1$-$C_5$ carboxyl, cyano, phenyl and benzyl,
m is an integer from 1 to 3 and
n is an integer from 1 to 3.

4. The two-photon probe compound for detecting copper (II) ion according to claim 3, wherein m is an integer from 1 to 2.

5. The two-photon probe compound for detecting copper (II) ion according to claim 3, wherein n is an integer from 1 to 2.

6. A method for preparing the compound according to claim 1 by reacting a compound of [Chemical Formula 5] with a compound of [Chemical Formula 6]:

[Chemical Formula 5]

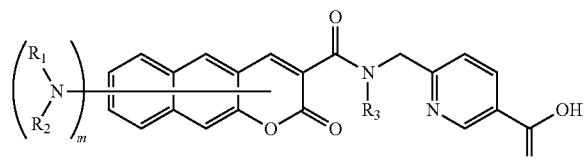

[Chemical Formula 6]

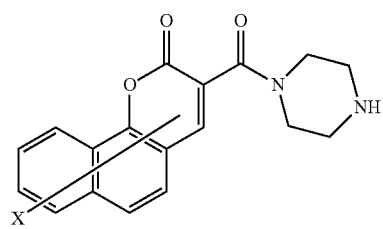

wherein
each of $R_1$, $R_2$ and $R_3$, which are identical or different, is independently hydrogen or $C_1$-$C_{10}$ substituted or unsubstituted alkyl,
X is —$OCH_2(CH_2OCH_2)_nCH_2OCH_3$,
the substituted alkyl is substituted with a substituent selected from a group consisting of halogen, trifluoromethyl amino, $C_1$-$C_5$ alkyl, $C_1$-$C_5$ alkoxy, hydroxyl, $C_1$-$C_5$ carboxyl, cyano, phenyl and benzyl and
m is an integer from 1 to 3 and
n is an integer from 1 to 6.

7. The method according to claim 6, wherein the compound of [Chemical Formula 5] is prepared by: preparing a compound of [Chemical Formula 9] by reacting a compound of [Chemical Formula 7] with a compound of [Chemical Formula 8]; and replacing the ester group of the [Chemical Formula 9] with a carboxyl group:

[Chemical Formula 7]

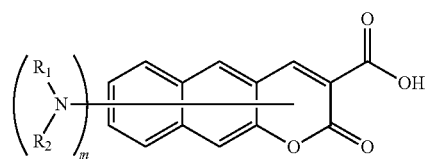

[Chemical Formula 8]

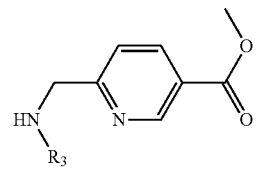

[Chemical Formula 9]

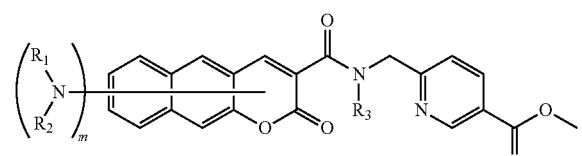

wherein
each of $R_1$, $R_2$ and $R_3$, which are identical or different, is independently hydrogen or $C_1$-$C_{10}$ substituted or unsubstituted alkyl,
the substituted alkyl is substituted with a substituent selected from a group consisting of halogen, trifluoromethyl, amino, $C_1$-$C_5$ alkyl, $C_1$-$C_5$ alkoxy, hydroxyl, $C_1$-$C_5$ carboxyl, cyano, phenyl and benzyl and
m is an integer from 1 to 3.

8. The method according to claim 6, wherein the compound of [Chemical Formula 6] is prepared by: preparing a compound of [Chemical Formula 11] by reacting a compound of [Chemical Formula 10] with piperazine having one amine group protected by an amine protecting group; and removing the amine protecting group from the compound of [Chemical Formula 11]:

[Chemical Formula 10]

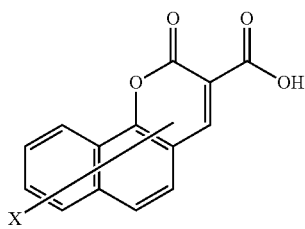

[Chemical Formula 11]

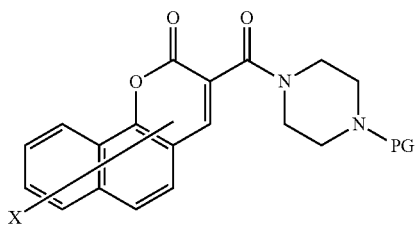

wherein PG is the amine protecting group.

9. A method for quantitatively estimating copper(II) ion concentration in vivo using the ratio of emission intensities measured in short wavelength and long wavelength regions as a result of a reaction between a compound of [Chemical Formula 1] and copper(II) ion present in vivo:

m is an integer from 1 to 3 and n is an integer from 1 to 6.

10. The method for quantitatively estimating copper(II) ion concentration in vivo according to claim 9, wherein the distance between the maximum wavelength in the short wavelength region and the minimum wavelength in the long wavelength region is 70 nm or greater.

11. The method for quantitatively estimating copper(II) ion concentration in vivo according to claim 9, wherein the short wavelength region is 400-480 nm.

12. The method for quantitatively estimating copper(II) ion concentration in vivo according to claim 9, wherein the reaction between the compound of [Chemical Formula 1] and the copper(II) ion present in vivo is conducted at pH 5-7.5.

13. method for quantitatively estimating copper(II) ion concentration in vivo according to claim 9, wherein the compound of [Chemical Formula 1] has a structure of [Chemical Formula 2]:

[Chemical Formula 1]

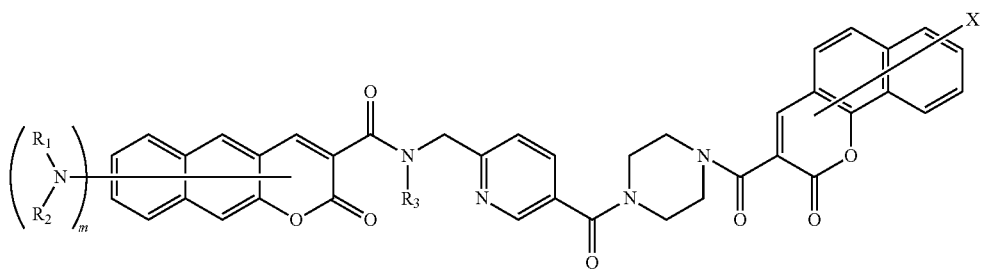

wherein each of $R_1$, $R_2$ and $R_3$, which are identical or different, is independently hydrogen or $C_1$-$C_{10}$ substituted or unsubstituted alkyl, X is —$OCH_2(CH_2OCH_2)CH_2OCH_3$, the substituted alkyl is substituted with a substituent selected from a group consisting of halogen, trifluoromethyl, amino, $C_1$-$C_5$ alkyl, $C_1$-$C_5$ alkoxy, hydroxyl, $C_1$-$C_5$ carboxyl, cyano, phenyl and benzyl and

[Chemical Formula 2]

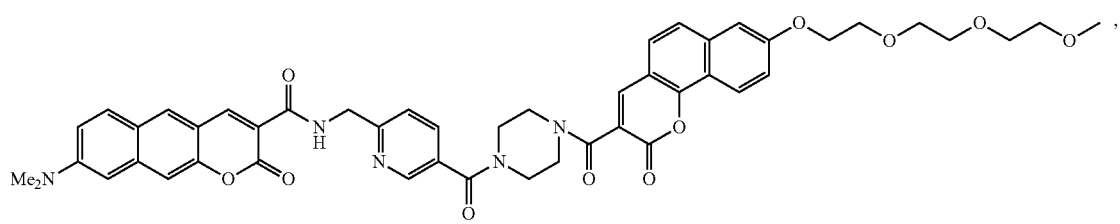

wherein Me stands for methyl.

* * * * *